(12) United States Patent
Nishiyama et al.

(10) Patent No.: US 7,189,877 B2
(45) Date of Patent: Mar. 13, 2007

(54) ARYLAMINE DERIVATIVES HAVING FLUORENE SKELETON, SYNTHETIC INTERMEDIATES THEREOF, PROCESSES OF PRODUCING THOSE, AND ORGANIC ELECTROLUMIVESCENE DEVICES

(75) Inventors: Masakazu Nishiyama, Shunan (JP); Hiroaki Tenma, Shunan (JP); Hisao Eguchi, Shunan (JP)

(73) Assignee: Tosch Corporation, Yamaguchi (JP)

( * ) Notice: Subject to any disclaimer, the term of this patent is extended or adjusted under 35 U.S.C. 154(b) by 677 days.

(21) Appl. No.: 10/663,683

(22) Filed: Sep. 17, 2003

(65) Prior Publication Data

US 2004/0110958 A1    Jun. 10, 2004

(30) Foreign Application Priority Data

| Sep. 20, 2002 | (JP) | ............ P. 2002-274983 |
| Jan. 10, 2003 | (JP) | ............ P. 2003-004818 |
| Feb. 28, 2003 | (JP) | ............ P. 2003-054070 |
| Jul. 18, 2003 | (JP) | ............ P. 2003-199203 |

(51) Int. Cl.
    *C07C 211/54*    (2006.01)
(52) U.S. Cl. ............ 564/315; 564/305; 564/322; 548/400
(58) Field of Classification Search ............ None
    See application file for complete search history.

(56) References Cited

U.S. PATENT DOCUMENTS

| 3,189,447 | A | | 6/1965 | Neugebauer et al. |
| 3,257,203 | A | | 6/1966 | Oskar et al. |
| 5,386,002 | A | * | 1/1995 | Inbasekaran et al. ....... 528/170 |
| 5,470,987 | A | * | 11/1995 | Inbasekaran ................ 548/462 |
| 5,698,740 | A | | 12/1997 | Enokida et al. |
| 6,479,172 | B2 | | 11/2002 | Hu et al. |
| 2002/0132134 | A1 | | 9/2002 | Hu et al. |

FOREIGN PATENT DOCUMENTS

| JP | 51-93224 A | 8/1976 |
| JP | 54-59143 A | 5/1979 |
| JP | 55-108667 A | 8/1980 |
| JP | 55-144250 A | 11/1980 |
| JP | 56-119132 A | 9/1981 |
| JP | 58-190953 A | 11/1983 |
| JP | 59-195658 A | 11/1984 |
| JP | 10-139742 A | 5/1998 |

OTHER PUBLICATIONS

Saa et al. Journal of Organic Chemistry 1993. 58. 1963-1966.*
O'Brien et al., "Hole Transporting Materials with High Glass Transition Temperatures for Use in Organic Light-Emitting Devices", Advanced Materials, (Germany), 1998, vol. 10, No. 14, pp. 1108-1112.
Shirota et al., "Starburst molecules based on η-electron systems as materials for organic electroluminescent devices" Journal of Luminescence, (Holland), 1997, 72-74, pp. 985-991.
XP-002266476—Ishida Tsutomu et al., "Diphenylfluorene derivatives and organic electroluminescence devices using them with high luminescence efficiency"—abstract of JP 2003 261472 A (Sep. 16, 2003).
European Search Report dated Jan. 28, 2004.

* cited by examiner

*Primary Examiner*—Thurman K. Page
*Assistant Examiner*—Yevgeny Valenrod
(74) *Attorney, Agent, or Firm*—Sughrue Mion, PLLC

(57) ABSTRACT

Arylamine derivatives that can be utilized as hole transport or hole injection materials of organic electroluminescence devices, electrophotographic reactors, etc., and synthetic intermediates thereof, and processes of producing those. The arylamine derivative is represented by the general formula (1):

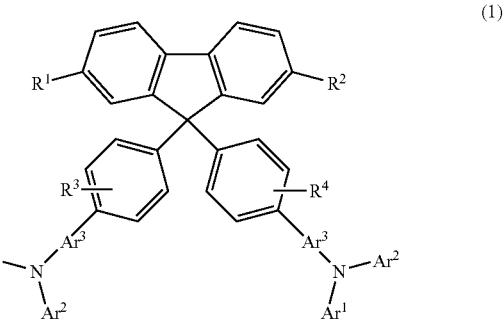

(1)

wherein $R^1$ to $R^4$ each independently represents a hydrogen atom, an alkyl group, an alkoxy group, an aryl group, an aryloxy group, a halogen atom, an amino group, etc.; $Ar^1$ and $Ar^2$ each independently represents a substituted or unsubstituted aryl group or hetero-aromatic group, and $Ar^1$ and $Ar^2$ may form a nitrogen-containing heterocyclic ring together with the nitrogen atom to which $Ar^1$ and $Ar^2$ bond; and $Ar^3$ represents a substituted or unsubstituted arylene group.

21 Claims, 1 Drawing Sheet

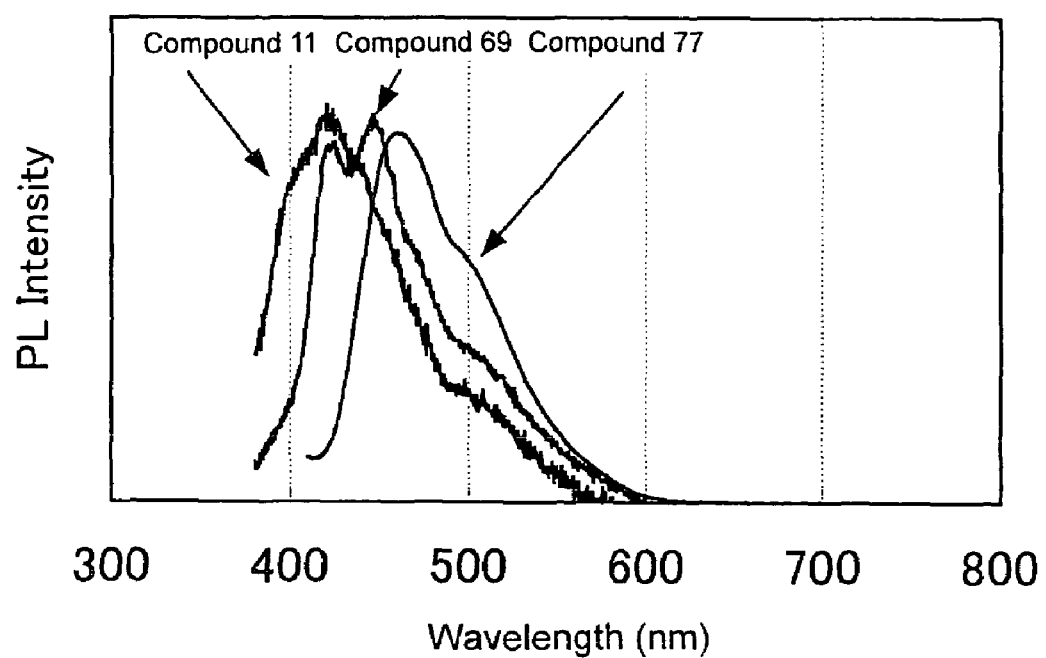

ARYLAMINE DERIVATIVES HAVING FLUORENE SKELETON, SYNTHETIC INTERMEDIATES THEREOF, PROCESSES OF PRODUCING THOSE, AND ORGANIC ELECTROLUMIVESCENE DEVICES

FIELD OF THE INVENTION

The present invention relates to novel arylamine derivatives having a fluorene skeleton, di(haloaryl)fluorene derivatives as synthetic intermediates thereof, processes of producing those, and organic electroluminescence (EL) devices. The novel arylamine derivatives having a fluorene skeleton can be used as photosensitive materials and organic photoconductive materials and more specifically, can be utilized as hole transport or hole injection materials and luminescent materials of organic EL devices used for planar light sources or displays, electrophotographic receptors, etc.

DESCRIPTION OF THE RELATED ART

Organic photoconductive materials that are developed as photosensitive materials or hole transport materials have many advantages such as low costs, variable processability, and non-pollution, and many compounds are proposed. For example, there are disclosed materials such as oxadiazole derivatives (for example, U.S. Pat. No. 3,189,447), oxazole derivatives (for example, U.S. Pat. No. 3,257,203), hydrazone derivatives (for example, JP-A-54-59143), triarylpyrazoline derivatives (for example, JP-A-51-93224 and 55-108667), arylamine derivatives (for example, JP-A-55-144250 and 56-119132), and stilbene derivatives (for example, JP-A-58-190953 and 59-195658).

Above all, arylamine derivatives such as 4,4',4''-tris-[N,N-(1-naphthyl)phenylamino]triphenylamine (1-TNATA), 4,4',4''-tris[N,N-(m-tolyl)phenylamino]triphenylamine (MTDATA), 4,4'-bis[N-(1-naphthyl)-N-phenylamino]biphenyl (α-NPD), and 4,4'-bis[N-(m-tolyl)-N-phenylamino]biphenyl (TPD) are frequently used as hole transport or hole injection materials (*Advanced Materials*, (Germany), 1998, Vol. 10, No. 14, pp.1108–1112 (FIG. 1 and Table 1), and *Journal of Luminescence*, (Holland), 1997, 72–74, pp.985–991 (FIG. 1)). However, since these materials have drawbacks such as poor stability and poor durability, development of hole transport materials having an excellent hole transport capability and a high Tg (=glass transition temperature) and having durability is desired at present.

Further, as a process of producing arylamines, there is known a method of using a catalyst comprising a trialkyiphosphine and a palladium compound in the amination reaction of aryl halides by an amine compound in the presence of a base, as described in, for example, JP-A-10-139742.

An object of the present invention is to provide novel materials having an excellent hole transport capability, having a Tg higher than α-NPD or MTDATA and having durability In particular, the present invention provides novel arylamine derivatives that are suitable for hole transport materials and luminescent materials of organic EL devices, etc.

SUMMARY OF THE INVENTION

The present inventors made extensive and intensive investigations. As a result, it has been found that arylamine derivatives represented by the following general formula (1) have a high Tg and can be utilized as a blue luminescent material, leading to accomplishment of the present invention. Specifically, the invention relates to a novel arylamine derivative having a fluorene skeleton represented by the general formula (1) and a process of producing the same and an organic EL device using a novel arylamine derivative having a fluorene skeleton represented by the general formula (1).

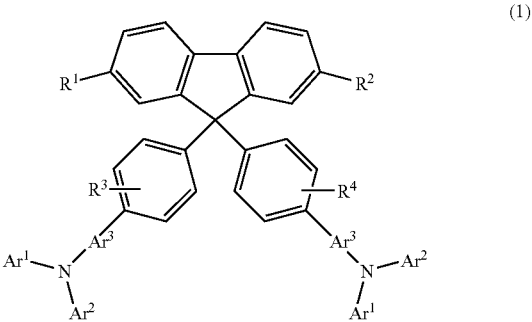

wherein $R^1$ to $R^4$ each independently represents a hydrogen atom, a linear, branched or cyclic alkyl group or alkoxy group, an aryl group, an aryloxy group, a halogen atom, an amino group, or a group represented by the following general formula (2), (3) or (4); $Ar^1$ and $Ar^2$ each independently represents a substituted or unsubstituted aryl group or hetero-aromatic group, and $Ar^1$ and $Ar^2$ may form a nitrogen-containing heterocyclic ring together with the nitrogen atom to which $Ar^1$ and $Ar^2$ bond; and $Ar^3$ represents a substituted or unsubstituted arylene group.

wherein Y represents a group represented by any one of the following general formulae (5a) to (5f); and W represents a hydrogen atom or a substituted or unsubstituted aryl group.

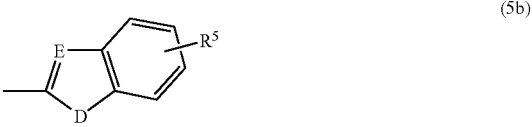

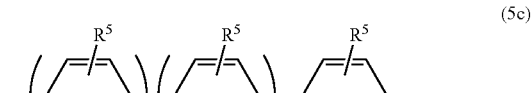

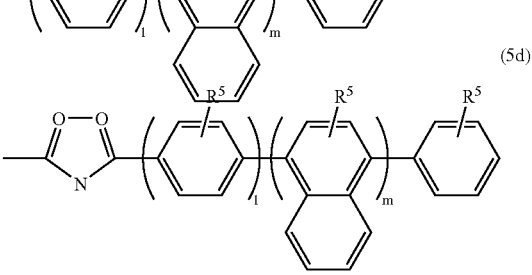

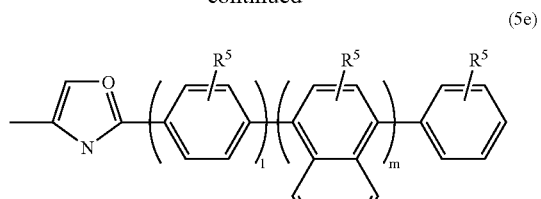

(5e)

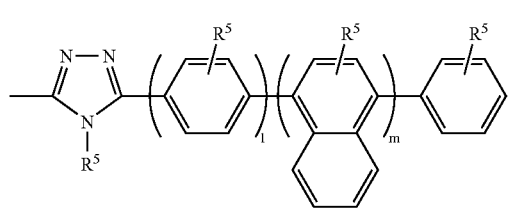

(5f)

wherein R⁵s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —CR⁶— or a nitrogen atom; D represents any one of an oxygen atom, a nitrogen atom, or a sulfur atom; R⁶ represents a hydrogen atom, a linear, branched or cyclic alkyl group, an aryl group, an amino group, a cyano group, a nitro group, a hydroxyl group, or a halogen atom; and l and m each represents an integer of from 0 to 4, satisfying the relation of (l+m)≦4.

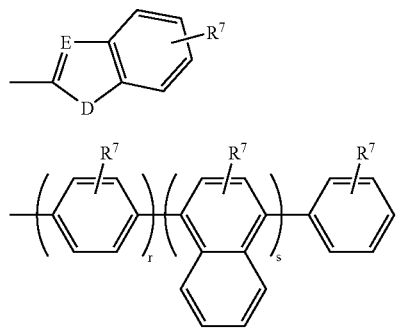

(3)

(4)

wherein R⁷s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —CR⁸— or a nitrogen atom; R⁸ represents a hydrogen atom, a linear, branched or cyclic alkyl group, an aryl group, an amino group, a cyano group, a nitro group, a hydroxyl group, or a halogen atom; D represents any one of an oxygen atom, a nitrogen atom, or a sulfur atom; and r and s each represents an integer of from 0 to 4, satisfying the relation of (r+s)≦4.

The present invention further relates to a di(haloaryl) fluorene derivative represented by the following general formula (8), which is a synthetic intermediate of the arylamine derivative represented by the foregoing general formula (1), and a process of producing the same.

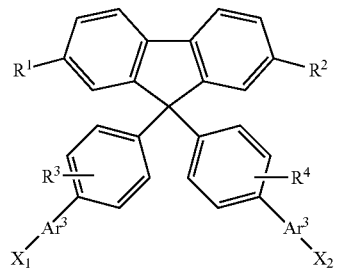

(8)

wherein R¹ to R⁴ and Ar³ each represents the same substituent as defined previously; and X¹ and X² each represents a chlorine atom, a bromine atom, or an iodine atom.

BRIEF DESCRIPTION OF THE DRAWING

The FIGURE shows PL measurement results of thin film with respect to Compounds 11, 69 and 77.

DETAILED DESCRIPTION OF THE INVENTION

The present invention will be described in detail below.
In the arylamine derivative represented by the general formula (1), Ar¹ and Ar² each independently represents a substituted or unsubstituted aryl group or hetero-aromatic group, and Ar¹ and Ar² may form a nitrogen-containing heterocyclic ring together with the nitrogen atom to which Ar¹ and Ar² bond.

The substituted or unsubstituted aryl groups are optionally substituted aromatic groups having from 6 to 24 carbon atoms. Specific examples include a phenyl group, a 1-naphthyl group, a 2-naphthyl group, a 2-anthryl group, a 9-anthryl group, a 2-fluorenyl group, a 4-methylphenyl group, a 3-methylphenyl group, a 2-methylphenyl group, a 4-ethylphenyl group, a 3-ethylphenyl group, a 2-ethylphenyl group, a 4-n-propylphenyl group, a 4-isopropylphenyl group, a 2-isopropylphenyl group, a 4-n-butylphenyl group, a 4-isobutylphenyl group, a 4-sec-butylphenyl group, a 2-sec-butylphenyl group, a 4-tert-butylphenyl group, a 3-tert-butylphenyl group, a 2-tert-butylphenyl group, a 4-n-pentylphenyl group, a 4-isopentylphenyl group, a 2-neopentylphenyl group, a 4-tert-pentylphenyl group, a 4-n-hexylphenyl group, a 4-(2'-ethylbutyl)phenyl group, a 4-n-heptylphenyl group, a 4-n-octylphenyl group, a 4-(2'-ethylhexyl)phenyl group, a 4-tert-octylphenyl group, a 4-n-decylphenyl group, a 4-n-dodecylphenyl group, a 4-n-tetradecylphenyl group, a 4-cyclopentylphenyl group, a 4-cyclohexylphenyl group, a 4-(4'-methylcyclohexyl)phenyl group, 4-(4'-tert-butylcyclohexyl)phenyl group, a 3-cyclohexylphenyl group, a 2-cyclohexylphenyl group, a 4-ethyl-1-naphthyl group, a 6-n-butyl-2-naphthyl group, a 2,4-dimethylphenyl group, 2,5-dimethylphenyl group, a 3,4-dimethylphenyl group, a 3,5-dimethylphenyl group, a 2,6-dimethylphenyl group, a 2,4-diethylphenyl group, a 2,3,5-trimethylphenyl group, a 2,3,6-trimethylphenyl group, a 3,4,5-trimethylphenyl group, a 2,6-diethylphenyl group, a 2,5-diisopropylphenyl group, a 2,6-diisobutylphenyl group, a 2,4-di-tert-butylphenyl group, a 2,5-di-tert-butylphenyl group, a 4,6-di-tert-butyl-2-methylphenyl group, a 5-tert-butyl-2-methylphenyl group, a 4-tert-butyl-2,6-dimethylphenyl group, a 9-methyl-2-fluorenyl group, a 9-ethyl-2-fluorenyl group, a 9-n-hexyl-2-fluorenyl group, a 9,9-dimethyl-2-fluorenyl group, a 9,9-diethyl-2-fluorenyl group, a 9,9-di-n-propyl-2-fluorenyl group, a 4-methoxyphenyl group, a 3-methoxyphenyl group, a 2-methoxyphenyl group, a 4-ethoxyphenyl group, a 3-ethoxyphenyl group, a 2-ethoxyphenyl group, a 4-n-propoxyphenyl group, a 3-n-propoxyphenyl group, a 4-isopropoxyphenyl group, a 2-isopropoxyphenyl group, a 4-n-butoxyphenyl group, a 4-isobutoxyphenyl group, a 2-sec-butoxyphenyl group, a 4-n-pentyloxyphenyl group, a 4-isopentyloxyphenyl group, a 2-isopentyloxyphenyl group, a 4-neopentyloxyphenyl group, a 2-neopentyloxyphenyl group, a 4-n-hexyloxyphenyl group, a 2-(2'-ethylbutyl)oxyphenyl group, 4-n-octyloxyphenyl group, a 4-n-decyloxyphenyl group, a 4-n-dodecyloxyphenyl group, a 4-n-tetradecyloxyphenyl group, a 4-cyclohexyloxyphenyl group, a 2-cyclohexyloxyphenyl group, a 2-methoxy-1-naphthyl group, a 4-methoxy-1-naphthyl group, a 4-n-butoxy-1-naphthyl group, a 5-ethoxy-1-naphthyl group, a 6-methoxy-2-naphthyl group, a 6-ethoxy-2-naphthyl group, a 6-n-butoxy-2-naphthyl group, a 6-n-hexyloxy-2-naphthyl group, a 7-methoxy-2-naphthyl group, a 7-n-butoxy-2-naphthyl group, a 2-methyl-4-methoxyphenyl group, a 2-methyl-5-methoxyphenyl group, a 3-methyl-4-methoxyphenyl group, a 3-methyl-5-methoxyphenyl group, a 3-ethyl-5-methoxyphenyl group, a 2-methoxy-4-methylphenyl group, a 3-methoxy-4-methylphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,5-diethoxyphenyl group, a 3,5-di-n-butoxyphenyl group, a 2-methoxy-4-ethoxyphenyl group, a 2-methoxy-6-ethoxyphenyl group, a 3,4,5-tri-methoxyphenyl group, a 4-phenylphenyl group, a 3-phenylphenyl group, a 2-phenylphenyl group, a 4-(4'-methylphenyl)phenyl group, a 4-(3'-methylphenyl)phenyl group, a 4-(4'-methoxyphenyl)phenyl group, a 4-(4'-n-butoxyphenyl)phenyl group, a 2-(2'-methoxyphenyl)phenyl group, a 4-(4'-chlorophenyl)phenyl group, a 3-methyl-4-phenylphenyl group, a 3-methoxy-4-phenylphenyl group, a 9-phenyl-2-fluorenyl group, a 4-fluorophenyl group, a 3-fluorophenyl group, a 2-fluorophenyl group, a 4-chlorophenyl group, a 3-chlorophenyl group, a 2-chlorophenyl group, a 4-bromophenyl group, a 2-bromophenyl group, a 4-chloro-1-naphthyl group, a 4-chloro-2-naphthyl group, a 6-bromo-2-naphthyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2,5-dibromophenyl group, a 2,4,6-trichlorophenyl group, a 2,4-dichloro-1-naphthyl group, a 1,6-dichloro-2-naphthyl group, a 2-fluoro-4-methylphenyl group, a 2-fluoro-5-methylphenyl group, a 3-fluoro-2-methylphenyl group, a 3-fluoro-4-methylphenyl group, a 2-methyl-4-fluorophenyl group, a 2-methyl-5-fluorophenyl group, a 3-methyl-4-fluorophenyl group, a 2-chloro-4-methylphenyl group, a 2-chloro-5-methylphenyl group, a 2-chloro-6-methylphenyl group, a 2-methyl-3-chlorophenyl group, a 2-methyl-4-chlorophenyl group, a 3-chloro-4-methylphenyl group, a 3-methyl-4-chlorophenyl group, a 2-chloro-4,6-dimethylphenyl group, a 2-methoxy-4-fluorophenyl group, a 2-fluoro-4-methoxyphenyl group, a 2-fluoro-4-ethoxyphenyl group, a 2-fluoro-6-methoxyphenyl group, a 3-fluoro-4-ethoxyphenyl group, a 3-chloro-4-methoxyphenyl group, a 2-methoxy-5-chlorophenyl group, a 3-methoxy-6-chlorophenyl group, and a 5-chloro-2,4-dimethoxyphenyl group. However, it should not be construed that the invention is limited thereto.

The substituted or unsubstituted hetero-aromatic groups are aromatic groups containing at least one hetero atom of an oxygen atom, a nitrogen atom, and a sulfur atom. Examples thereof include a 4-quinolyl group, a 4-pyridyl group, a 3-pyridyl group, a 2-pyridyl group, a 3-furyl group, a 2-furyl group, a 3-thienyl group, a 2-thienyl group, a 2-oxazolyl group, a 2-thiazolyl group, a 2-benzoxazolyl group, a 2-benzothiazolyl group, and a 2-benzoimidazolyl group. However, it should not be construed that the invention is limited thereto.

To attain a high Tg, it is preferable that at least one of $Ar^1$ and $Ar^2$ represents a substituted or unsubstituted condensed ring aromatic group. Examples thereof include a naphthyl group, a phenanthryl group, a fluorenyl group, an anthracenyl group, a pyrenyl group, a chrysenyl group, a picenyl group, and a perillenyl group, with a 1-naphthyl group, a 9-phenanthryl group, and a 2-fluorenyl group being more preferable.

In the compounds represented by the general formula (1), $Ar^1$ and $Ar^2$ may form a nitrogen-containing heterocyclic ring together with the nitrogen atom to which $Ar^1$ and $Ar^2$ bond and may form a substituted or unsubstituted —N-carbazolyl group, —N-phenoxazinyl group or —N-phenothiazinyl group. The nitrogen-containing heterocyclic ring may be monosubstituted or polysubstituted with a substituent such as a halogen atom, an alkyl group having from 1 to 10 carbon atoms, an alkoxy group having from 1 to 10 carbon atoms, and an aryl group having from 6 to 10 carbon atoms. Above all, an unsubstituted —N-carbazolyl group, —N-phenoxazinyl group or —N-phenothiazinyl group, or —N-carbazolyl groups, —N-phenoxazinyl groups or —N-phenothiazinyl groups monosubstituted or polysubstituted with a halogen atom, an alkyl group having from 1 to 4 carbon atoms, an alkoxy group having from 1 to 4 carbon atoms, or an aryl group having from 6 to 10 carbon atoms are preferable, with unsubstituted —N-carbazolyl groups, —N-phenoxazinyl groups or —N-phenothiazinyl groups being more preferable. Specific examples of substituted —N-carbazolyl groups, —N-phenoxazinyl groups and —N-phenothiazinyl groups include a 2-methyl-N-carbazolyl group, a 3-methyl-N-carbazolyl group, a 4-methyl-N-carbazolyl group, a 3-n-butyl-N-carbazolyl group, a 3-n-hexyl-N-carbazolyl group, a 3-n-octyl-N-carbazolyl group, a 3-n-decyl-N-carbazolyl group, a 3,6-dimethyl-N-carbazolyl group, a 2-methoxy-N-carbazolyl group, a 3-methoxy-N-carbazolyl group, a 3-ethoxy-N-carbazolyl group, a 3-isopropoxy-N-carbazolyl group, a 3-n-butoxy-N-carbazolyl group, a 3-n-octyloxy-N-carbazolyl group, a 3-n-decyloxy-N-carbazolyl group, a 3-phenyl-N-carbazolyl group, a 3-(4'-methylphenyl)-N-carbazolyl group, a 3-(4'-tert-butylphenyl)-N-carbazolyl group, a 3-chloro-N-carbazolyl group, and a 2-methyl-N-phenothiazinyl group.

In the arylamine derivatives represented by the general formula (1), $R^1$ to $R^4$ each independently represents a hydrogen atom, a linear, branched or cyclic alkyl group or alkoxy group, an aryl group, an aryloxy group, a halogen atom, an amino group, or a group represented by the following general formula (2), (3) or (4).

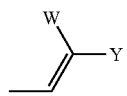

(2)

wherein Y represents a group represented by any one of the following general formulae (5a) to (5f), and W represents a hydrogen atom or a substituted or unsubstituted aryl group.

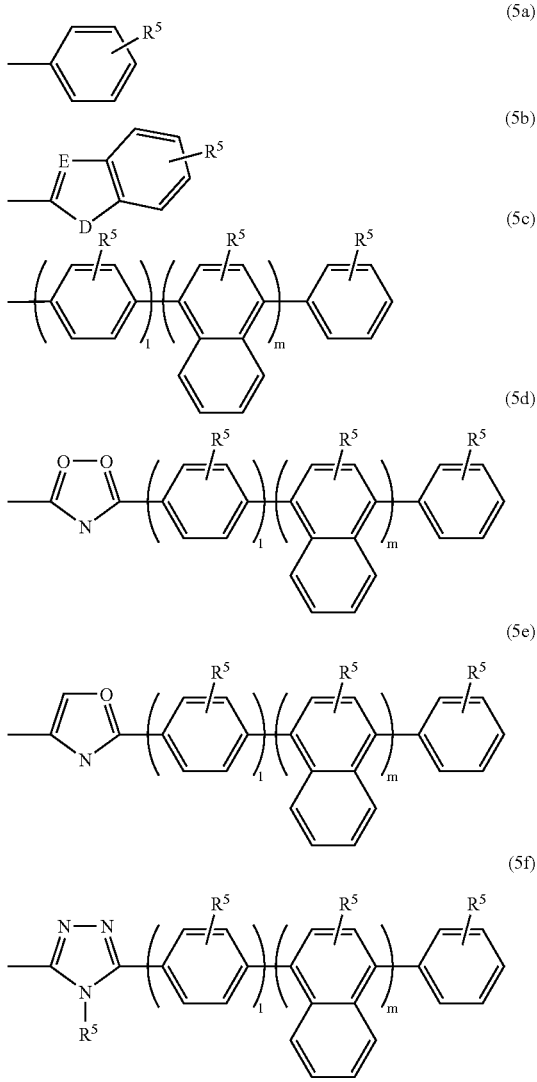

wherein R⁵s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —CR⁶— or a nitrogen atom; D represents any one of an oxygen atom, a nitrogen atom, or a sulfur atom; R⁶ represents a hydrogen atom, a linear, branched or cyclic alkyl group, an aryl group, an amino group, a cyano group, a nitro group, a hydroxyl group, or a halogen atom; and l and m each represents an integer of from 0 to 4, satisfying the relation of (l+m)≦4.

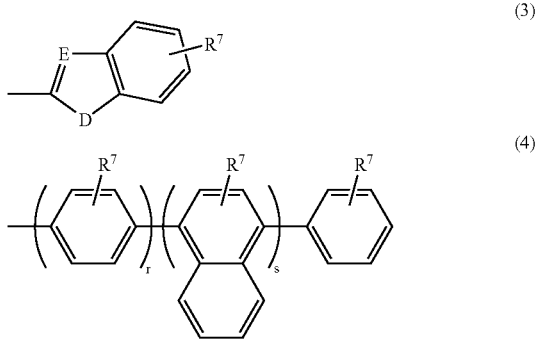

wherein R⁷s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —CR⁸— or a nitrogen atom; R⁸ represents a hydrogen atom, a linear, branched or cyclic alkyl group, an aryl group, an amino group, a cyano group, a nitro group, a hydroxyl group, or a halogen atom; D represents any one of an oxygen atom, a nitrogen atom, or a sulfur atom; and r and s each represents an integer of from 0 to 4, satisfying the relation of (r+s)≦4.

Examples of the alkyl group represented by R¹ to R⁸ include linear, branched or cyclic alkyl groups having from 1 to 18 carbon atoms. Specific examples include a methyl group, an ethyl group, a propyl group, an isopropyl group, a butyl group, a sec-butyl group, a tert-butyl group, a pentyl group, a hexyl group, a heptyl group, an octyl group, a stearyl group, a trichloromethyl group, a trifluoromethyl group, a cyclopropyl group, a cyclohexyl group, a 1,3-cyclohexadienyl group, and a 2-cyclopenten-1-yl group.

Examples of the alkoxy group represented by R¹ to R⁵ and R⁷ include linear, branched or cyclic alkoxy groups having from 1 to 18 carbon atoms. Specific examples include a methoxy group, an ethoxy group, a propoxy group, an isopropoxy group, an n-butoxy group, a sec-butoxy group, a tert-butoxy group, a pentyloxy group, a hexyloxy group, a stearyloxy group, and a trifluoromethoxy group.

Examples of the aryl group represented by R¹ to R⁸ and W include optionally substituted aryl groups having from 6 to 24 carbon atoms. Specific examples include the same substituents as described previously for Ar¹ or Ar², such as a phenyl group, a 4-methylphenyl group, a 3-methylphenyl group, a 2-methylphenyl group, a 4-ethylphenyl group, a 3-ethylphenyl group, a 2-ethylphenyl group, a 4-n-propylphenyl group, a 4-n-butylphenyl group, a 4-isobutylphenyl group, a 4-tert-butylphenyl group, a 4-cyclopentylphenyl group, a 4-cyclohexylphenyl group, a 2,4-dimethylphenyl group, a 3,5-dimethylphenyl group, a 3,4-dimethylphenyl group, a 4-(1-naphthyl)phenyl group, a 4-(9-anthryl)phenyl group, a 4-(10-phenyl-9-anthryl)phenyl group, a 4-biphenyl group, a 1-naphthyl group, a 2-naphthyl group, a 9-phenanthryl group, a 9-anthryl group, a 10-phenyl-9-anthryl group, a 10-biphenyl-9-anthryl group, a 9,9-dimethyl-fluoren-2-yl group, a 7-phenyl-9,9-dimethyl-fluoren-2-yl group, and a 9-di-trifluoromethyl-fluoren-2-yl group.

Examples of the aryloxy group represented by R¹ to R⁵ and R⁷ include optionally substituted aromatic groups having from 6 to 24 carbon atoms. Specific examples include a phenoxy group, a p-tert-butylphenoxy group, a 3-fluorophenoxy group, and a 4-fluorophenoxy group.

Examples of the halogen atom represented by R¹ to R⁸ include a fluorine atom, a chlorine atom, a bromine atom, and an iodine atom.

Examples of the amino group represented by R¹ to R⁸ include monosubstituted amino groups such as a methylamino group, an ethylamino group, a phenylamino group, an m-tolyl amino group, a p-tolyl amino group, a 1-naphthylamino group, a 2-naphthylamino group, and a 4-biphenylamino group; and disubstituted amino groups such as a dimethylamino group, a diethylamino group, a dipropylamino group, a dibutylamino group, a diphenylamino group, a di(m-tolyl)amino group, a di(p-tolyl)amino group, an N-(m-tolyl)phenylamino group, an N-(p-tolyl)phenylamino group, an N-(1-naphthyl)phenylamino group, an N-(2-naphthyl)phenylamino group, an N-(4-biphenyl)phe nylamino group, a di(4-biphenyl)amino group, a di(2-naphthyl)amino group, a bis(acetoxymethyl)amino group, a bis(acetoxyethyl)amino group, a bis(acetoxypropyl)amino group, a bis(acetoxybutyl)amino group, and a dibenzylamino group. However, it should not be construed that the invention is limited to these specific substituents.

The arylamine derivatives represented by the foregoing general formula (1) of the invention can be also utilized as a luminescent material because they have strong blue fluorescence. Especially, it is preferable that $R^1$ and $R^2$ in the general formula (1) each represents the group represented by the foregoing general formula (2), (3) or (4). In the case where $R^1$ and $R^2$ each represents the group represented by the general formula (2), it is further preferable that in the formula, Y is represented by any one of the foregoing general formulae (5a) to (5c), and W represents a hydrogen atom or an unsubstituted phenyl group. Moreover, it is preferable that Y is represented by any one of the following general formulae (7a) to (7c) and/or W represents a hydrogen atom. In the case where $R^1$ and $R^2$ each represents the group represented by the foregoing general formula (3), it is preferable that E in the formula represents —CH—, and D represents a sulfur atom.

(7a)

(7b)

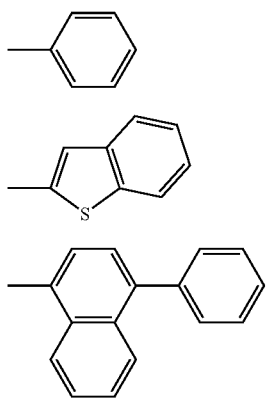

(7c)

In the arylamine derivatives represented by the general formula (1), $Ar^3$ is not particularly limited so far as it represents a substituted or unsubstituted arylene group, but is preferably an arylene group represented by any one of the following general formulae (14a) to (14e).

(14a)

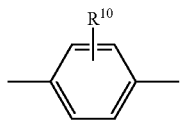

wherein $R^{10}$ represents a hydrogen atom, a halogen atom, a linear, branched or cyclic alkyl group or alkoxy group, or a substituted or unsubstituted aryl group.

(14b)

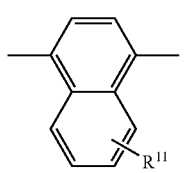

wherein $R^{11}$ represents a hydrogen atom, a halogen atom, a linear, branched or cyclic alkyl group or alkoxy group, or a substituted or unsubstituted aryl group.

(14c)

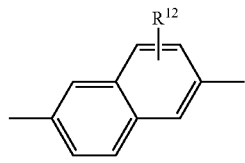

wherein $R^{12}$ represents a hydrogen atom, a halogen atom, a linear, branched or cyclic alkyl group or alkoxy group, or a substituted or unsubstituted aryl group.

(14d)

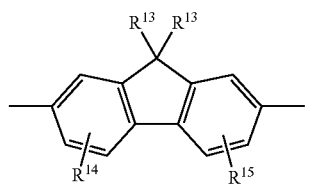

(14e)

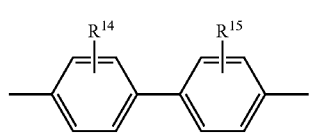

wherein $R^{13}$ to $R^{15}$ each independently represents a hydrogen atom, a halogen atom, a linear, branched or cyclic alkyl group or alkoxy group, or a substituted or unsubstituted aryl group.

Specific examples of $R^{10}$ to $R^{15}$ can be the same substituents as described previously for $R^1$ to $R^4$, $Ar^1$ and $Ar^2$. Of the arylene groups represented by the foregoing general formulae (14a) to (14e), those represented by the general formula (14a), especially a phenyl group, are particularly preferable because of easiness of availability of the raw materials from the viewpoint of synthesis.

Arylamine derivatives wherein $Ar^3$ represents a phenylene group, and $R^3$ and $R^4$ each represents a hydrogen atom, as represented by the following general formula (6), are also preferable.

(6)

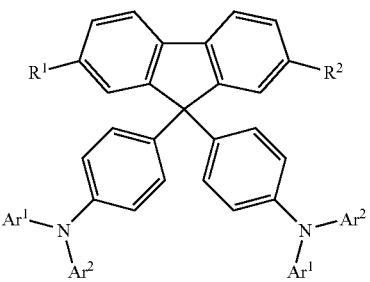

Preferable examples of compounds of the arylamine derivatives represented by the foregoing general formula (1) of the invention are shown in Tables 1 to 5, but it should not be construed that the invention is limited to the group of these compounds.

TABLE 1
| Compound | R¹ | R² | R³ | R⁴ | Ar³ | Ar¹ | Ar² |
|---|---|---|---|---|---|---|---|
| 1 | H | H | H | H |  |  |  |
| 2 | H | H | H | H |  |  |  |
| 3 | H | H | H | H |  |  |  |
| 4 | H |  | H | H |  |  |  |
| 5 | H | H | H | H |  | | |

TABLE 1-continued
| Compound | R¹ | R² | R³ | R⁴ | Ar³ | Ar¹ | Ar² |
|---|---|---|---|---|---|---|---|
| 6 | H | H | H | H | 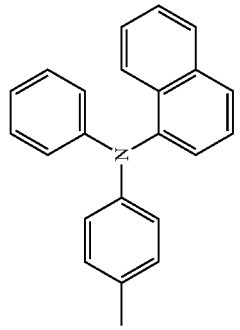 | 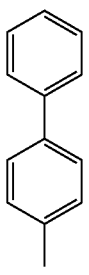 | 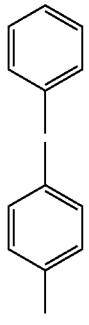 |
| 7 | H | H | H | H | 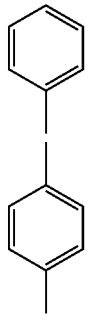 | 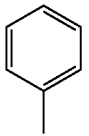 | 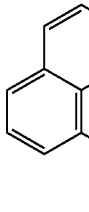 |
| 8 | 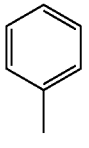 | 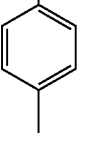 | H | H | 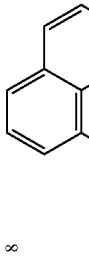 | 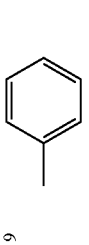 | 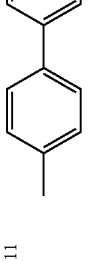 |
| 9 | 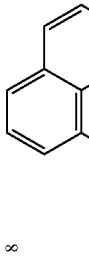 | 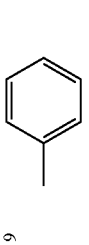 | H | H | 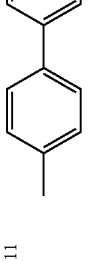 | | |
| 10 | 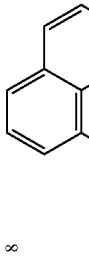 | 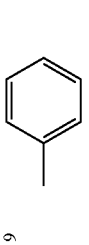 | H | H | | | |
| 11 | 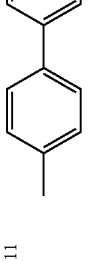 | 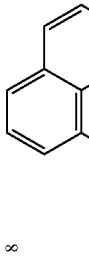 | H | H | | | |
| 12 | 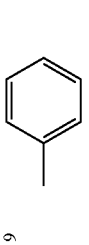 | 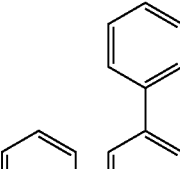 | H | H | | | |

TABLE 1-continued
| Compound | R$^1$ | R$^2$ | R$^3$ | R$^4$ | Ar$^3$ | Ar$^1$ | Ar$^2$ |
|---|---|---|---|---|---|---|---|
| 13 | 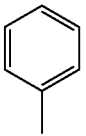 | 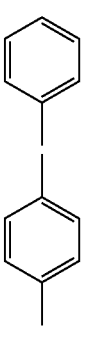 | H | H | 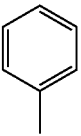 | 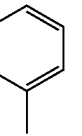 |  |
| 14 | 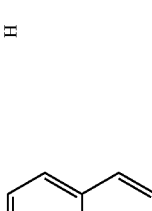 |  | H | H |  | 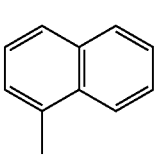 | 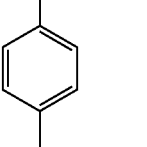 |
| 15 | 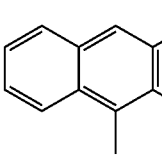 | 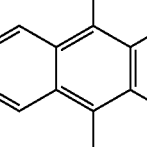 | H | H |  | 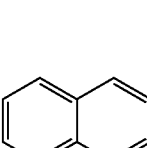 |  |
| 16 | 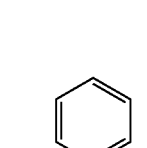 | | | | | | |

TABLE 1-continued
| Compound | R¹ | R² | R³ | R⁴ | Ar³ | Ar¹ | Ar² |
|---|---|---|---|---|---|---|---|
| 17 | 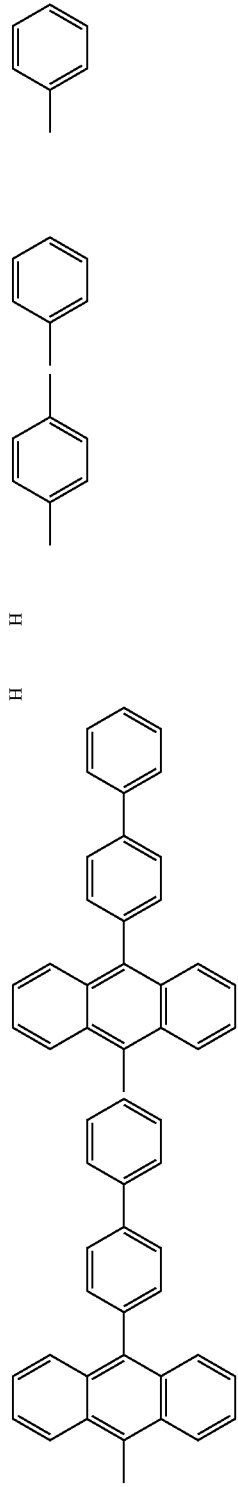 | | H | H | | | |
| 18 | H | H | 3-CH₃ | 3-CH₃ | 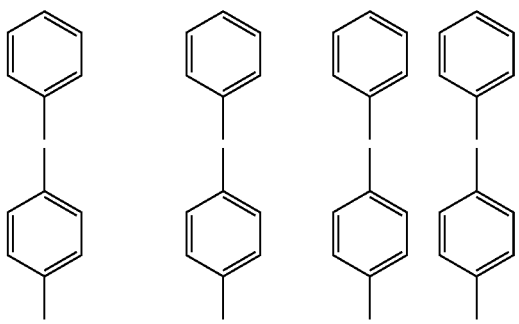 | | |
| 19 | H | H | 3-CH₃ | 3-CH₃ | | | |
| 20 | H | H | 3-CH₃ | 3-CH₃ | | | |
| 21 |  | 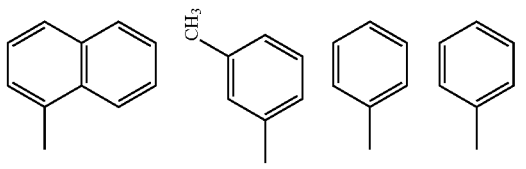 | 3-CH₃ | 3-CH₃ | | | |

TABLE 1-continued
| Compound | R¹ | R² | R³ | R⁴ | Ar³ | Ar¹ | Ar² |
|---|---|---|---|---|---|---|---|
| 22 | H | H | 3-CH₃ | 3-CH₃ | 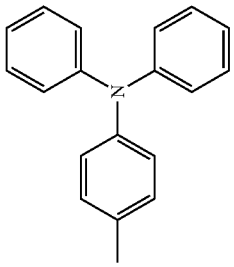 | 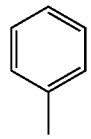 | 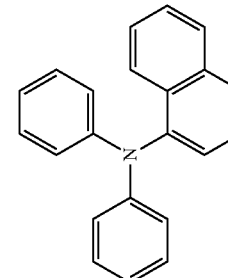 |
| 23 | H | H | | | | |  |
| 24 | H | H | 3-CH₃ | 3-CH₃ | | | |
| 25 | | | 3-CH₃ | 3-CH₃ | | | 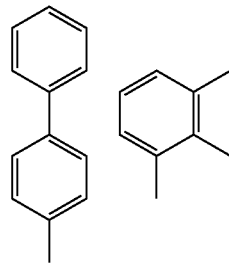 |
| 26 | | | 3-CH₃ | 3-CH₃ | | |  |

TABLE 1-continued
| Compound | R¹ | R² | Ar³ | Ar¹ | R³ | R⁴ | Ar² |
|---|---|---|---|---|---|---|---|
| 27 | 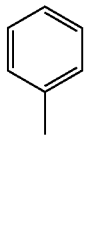 | 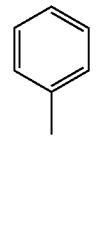 | 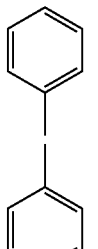 | | 3-CH₃ | 3-CH₃ | 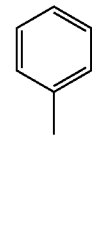 |
| 28 | 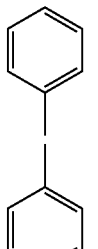 | 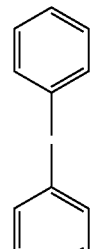 |  | | 3-CH₃ | 3-CH₃ |  |
| 29 |  | 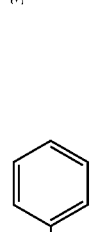 | 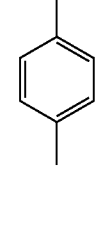 | | 3-CH₃ | 3-CH₃ | 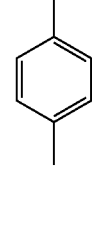 |
| 30 | 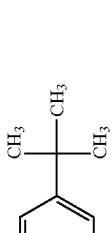 | | 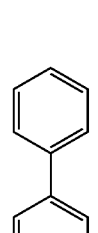 | | 3-CH₃ | 3-CH₃ | 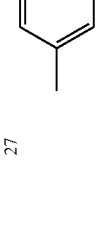 |
| 31 |  | | | | 3-CH₃ | 3-CH₃ | |

TABLE 1-continued
| Compound | R¹ | R² | R³ | R⁴ | Ar³ | Ar¹ | Ar² |
|---|---|---|---|---|---|---|---|
| 32 | 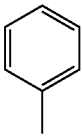 | 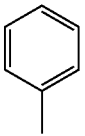 | | | | | |
| 33 | 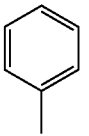 | 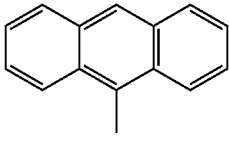 | 3-CH₃ | 3-CH₃ | 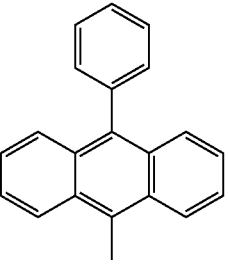 | 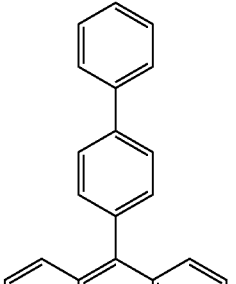 | 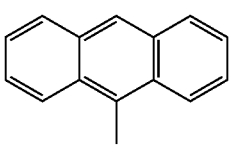 |
| 34 | 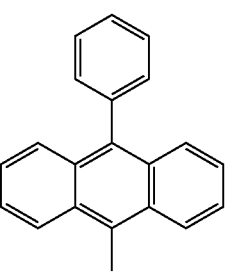 | 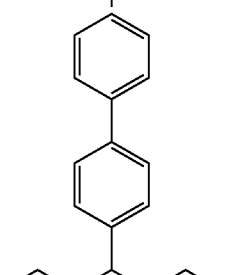 | 3-CH₃ | 3-CH₃ | | | |

TABLE 2
| Compound | R¹ | R² | R³ | R⁴ |
|---|---|---|---|---|
| 35 | H | H | H | H |
| 36 | H | H | H | H |
| 37 | H | H | H | H |
| 38 | 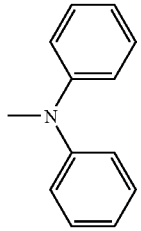 | 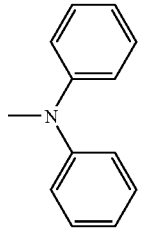 | H | H |
| 39 | H | H | H | H |
| 40 | H | H | H | H |
| 41 | H | H | H | H |
| 42 | 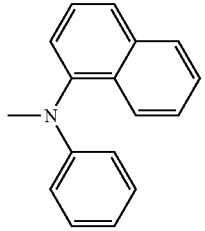 | 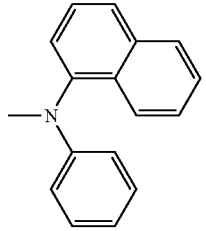 | H | H |
| 43 | 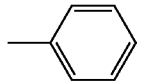 | 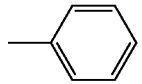 | H | H |
| 44 | 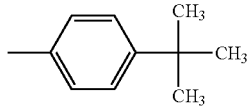 | 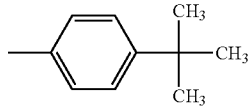 | H | H |
| 45 | 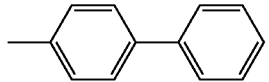 | 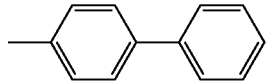 | H | H |
| 46 | 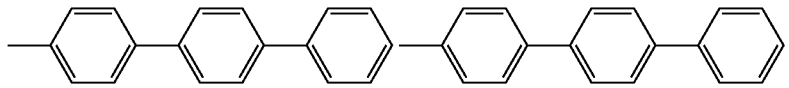 | | H | H |
| 47 | 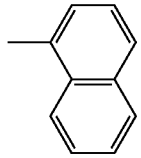 | 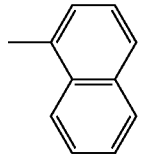 | H | H |
| 48 | 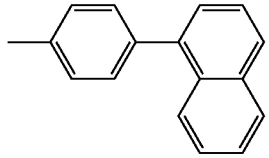 | 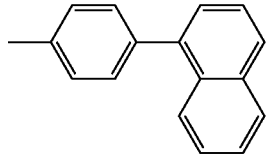 | H | H |

TABLE 2-continued

| # | (col A) | (col B) | (col C) | (col D) |
|---|---|---|---|---|
| 49 | 9-methylanthracenyl | 9-methylanthracenyl | H | H |
| 50 | 10-methyl-9-phenylanthracenyl | 10-methyl-9-phenylanthracenyl | H | H |
| 51 | 10-methyl-9-(biphenyl)anthracenyl | 9-(biphenyl)-10-(anthracenyl) | H | H |
| 52 | H | H | 3-CH$_3$ | 3-CH$_3$ |
| 53 | H | H | 3-CH$_3$ | 3-CH$_3$ |
| 54 | H | H | 3-CH$_3$ | 3-CH$_3$ |
| 55 | N,N-diphenylamino | N,N-diphenylamino | 3-CH$_3$ | 3-CH$_3$ |
| 56 | H | H | 3-CH$_3$ | 3-CH$_3$ |
| 57 | H | H | 3-CH$_3$ | 3-CH$_3$ |
| 58 | H | H | 3-CH$_3$ | 3-CH$_3$ |
| 59 | N-(1-naphthyl)-N-phenylamino | N-(1-naphthyl)-N-phenylamino | 3-CH$_3$ | 3-CH$_3$ |
| 60 | 4-methylphenyl | 4-methylphenyl | 3-CH$_3$ | 3-CH$_3$ |
| 61 | 4-tert-butylphenyl | 4-tert-butylphenyl | 3-CH$_3$ | 3-CH$_3$ |

TABLE 2-continued

| | Ar³ (structure) | Ar¹ (structure) | | |
|---|---|---|---|---|
| 62 | biphenyl | biphenyl | 3-CH₃ | 3-CH₃ |
| 63 | p-sexiphenyl (six-ring) | p-terphenyl | 3-CH₃ | 3-CH₃ |
| 64 | naphthyl | naphthyl | 3-CH₃ | 3-CH₃ |
| 65 | phenyl-naphthyl | phenyl-naphthyl | 3-CH₃ | 3-CH₃ |
| 66 | anthracenyl | anthracenyl | 3-CH₃ | 3-CH₃ |
| 67 | 10-phenylanthracenyl | 10-phenylanthracenyl | 3-CH₃ | 3-CH₃ |
| 68 | 10-(p-terphenyl)anthracenyl | 10-(p-terphenyl)anthracenyl | 3-CH₃ | 3-CH₃ |

| Compound | Ar³ | Ar¹ | Ar² |
|---|---|---|---|
| 35 | 9,9-dimethylfluorenyl | phenyl | 1-naphthyl |

TABLE 2-continued
| 36 | 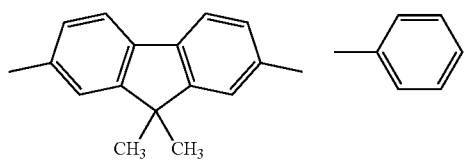 | 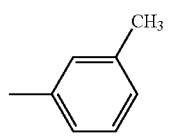 |
| --- | --- | --- |
| 37 | 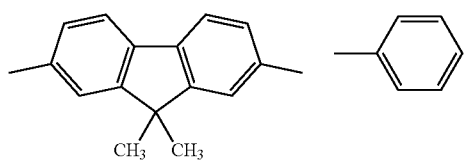 | 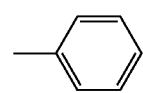 |
| 38 | 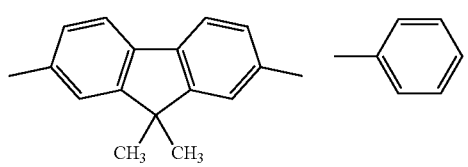 | 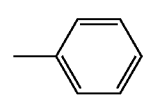 |
| 39 | 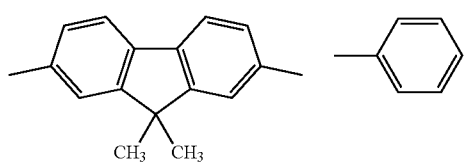 | 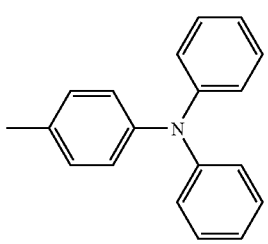 |
| 40 | 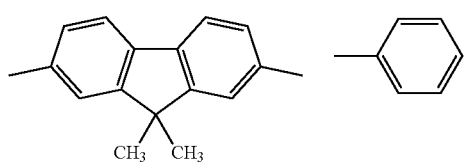 | 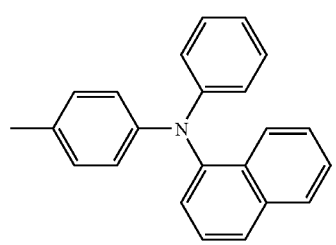 |
| 41 | 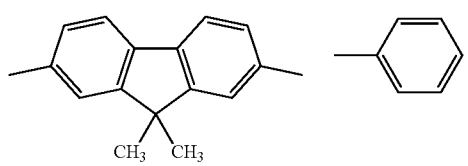 | 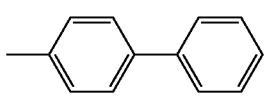 |
| 42 | 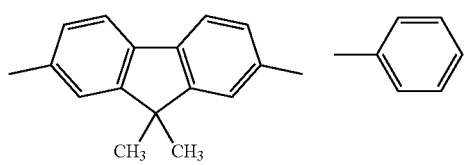 | 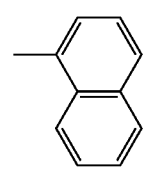 |
| 43 | 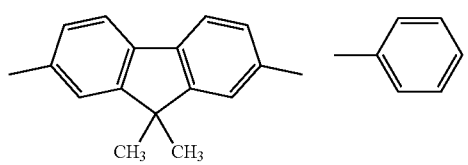 | 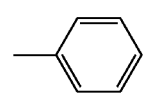 |

TABLE 2-continued

| | | | |
|---|---|---|---|
| 44 | 9,9-dimethylfluorene-2,7-diyl | phenyl | phenyl |
| 45 | 9,9-dimethylfluorene-2,7-diyl | phenyl | phenyl |
| 46 | 9,9-dimethylfluorene-2,7-diyl | phenyl | phenyl |
| 47 | 9,9-dimethylfluorene-2,7-diyl | phenyl | phenyl |
| 48 | 9,9-dimethylfluorene-2,7-diyl | phenyl | phenyl |
| 49 | 9,9-dimethylfluorene-2,7-diyl | phenyl | phenyl |
| 50 | 9,9-dimethylfluorene-2,7-diyl | phenyl | phenyl |
| 51 | 9,9-dimethylfluorene-2,7-diyl | phenyl | phenyl |
| 52 | 9,9-dimethylfluorene-2,7-diyl | phenyl | naphthyl |

TABLE 2-continued

| | | | |
|---|---|---|---|
| 53 | 2,7-dimethyl-9,9-dimethylfluorene | phenyl | 3-methylphenyl |
| 54 | 2,7-dimethyl-9,9-dimethylfluorene | phenyl | 2-methylphenyl |
| 55 | 2,7-dimethyl-9,9-dimethylfluorene | phenyl | phenyl |
| 56 | 2,7-dimethyl-9,9-dimethylfluorene | phenyl | 4-(N,N-diphenylamino)phenyl |
| 57 | 2,7-dimethyl-9,9-dimethylfluorene | phenyl | 4-(N-phenyl-N-1-naphthylamino)phenyl |
| 58 | 2,7-dimethyl-9,9-dimethylfluorene | phenyl | 4-biphenyl |
| 59 | 2,7-dimethyl-9,9-dimethylfluorene | phenyl | 1-naphthyl |
| 60 | 2,7-dimethyl-9,9-dimethylfluorene | phenyl | phenyl |

TABLE 2-continued
| | | | |
|---|---|---|---|
| 61 | 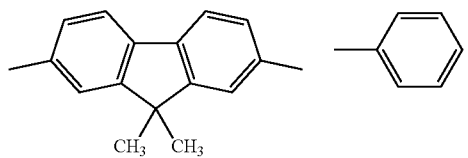 | 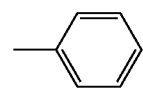 | |
| 62 | 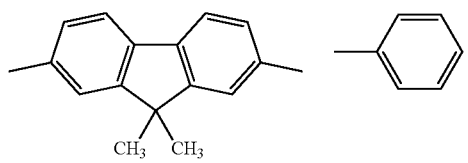 | 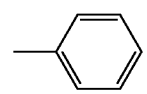 | |
| 63 | 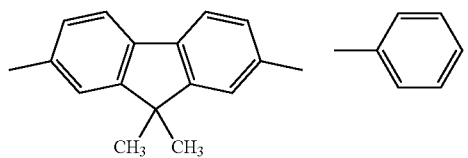 | 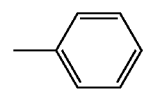 | |
| 64 | 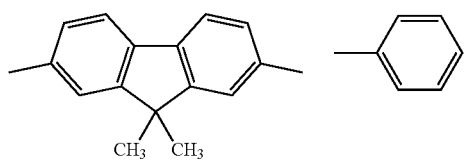 | 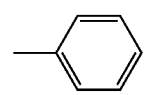 | |
| 65 | 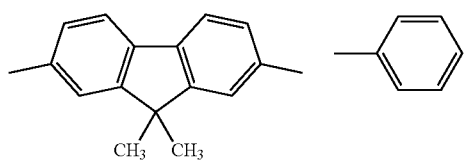 | 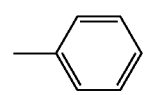 | |
| 66 | 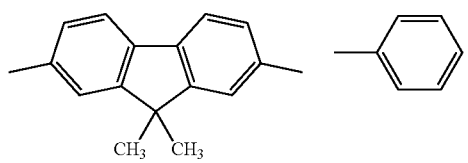 | 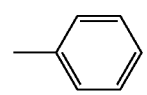 | |
| 67 | 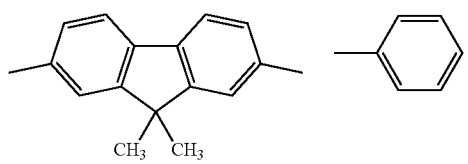 | 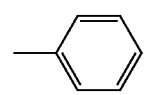 | |
| 68 | 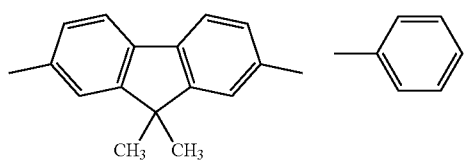 | 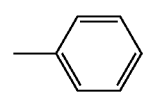 | |

TABLE 3
| Compound | R¹ | R² |
|---|---|---|
| 69 | 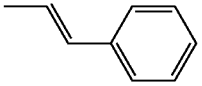 | 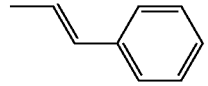 |
| 70 | 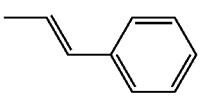 | 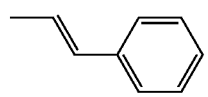 |
| 71 | 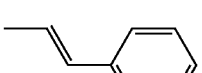 | 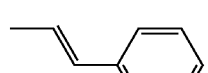 |
| 72 | 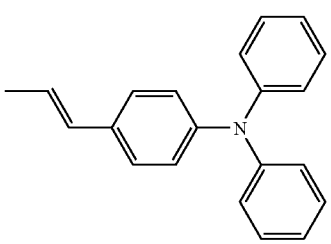 | 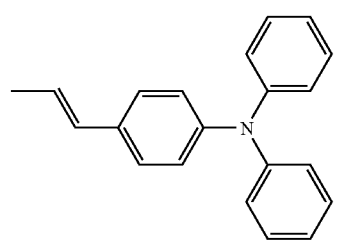 |
| 73 | 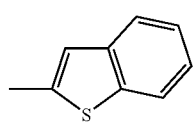 | 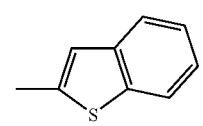 |
| 74 | 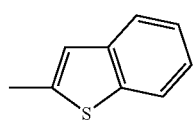 | 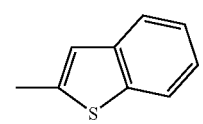 |
| 75 | 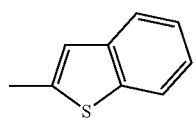 | 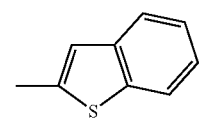 |
| 76 | 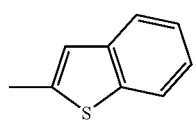 | 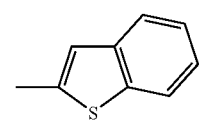 |
| 77 | 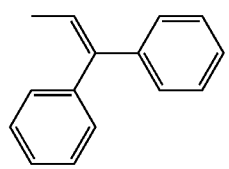 | 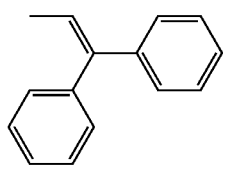 |
| 78 | 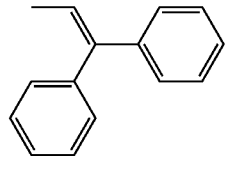 | 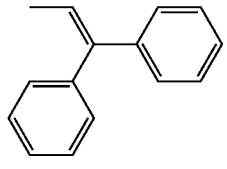 |
| 79 | 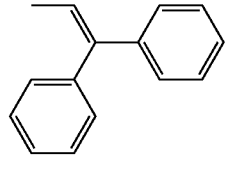 | 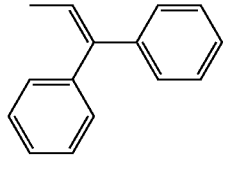 |

TABLE 3-continued
| | | |
|---|---|---|
| 80 | 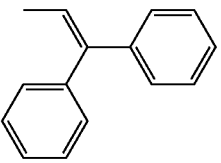 | 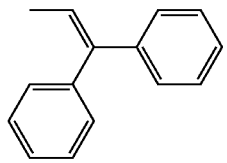 |
| 81 | 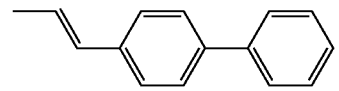 | 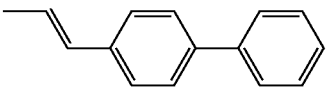 |
| 82 | 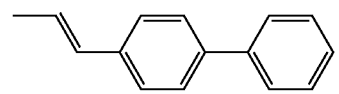 | 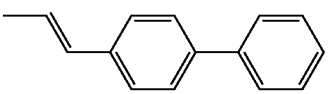 |
| 83 | 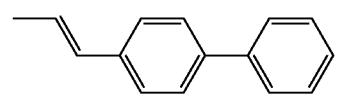 | 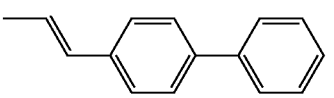 |
| 84 | 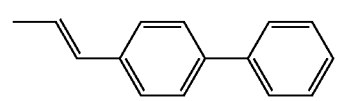 | 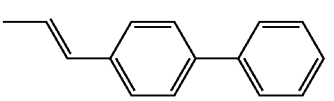 |
| 85 | 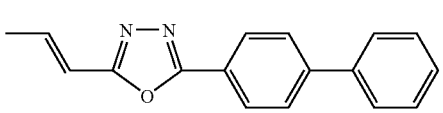 | 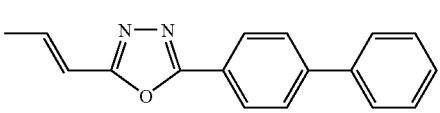 |
| 86 | 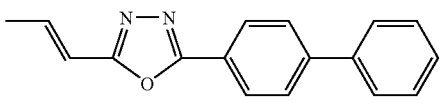 | 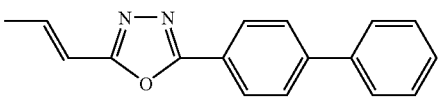 |
| 87 | 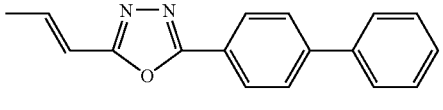 | 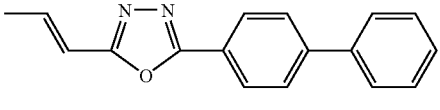 |
| 88 | 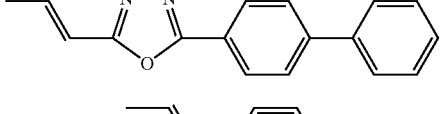 | 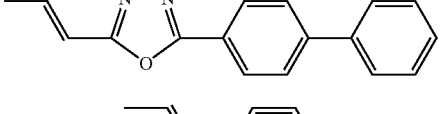 |
| 89 | 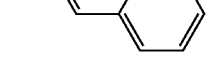 | 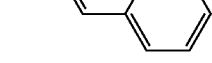 |
| 90 | 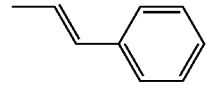 | 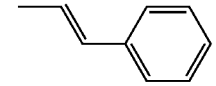 |
| 91 | 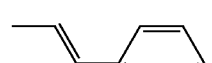 | 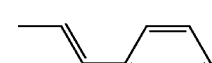 |
| 92 | 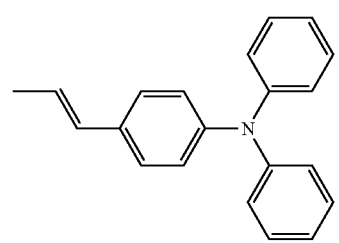 | 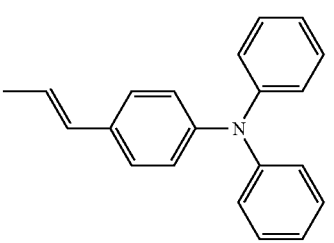 |

TABLE 3-continued

| | | |
|---|---|---|
| 93 | 2-methylbenzothiophene | 2-methylbenzothiophene |
| 94 | 2-methylbenzothiophene | 2-methylbenzothiophene |
| 95 | 2-methylbenzothiophene | 2-methylbenzothiophene |
| 96 | 2-methylbenzothiophene | 2-methylbenzothiophene |
| 97 | 1,1-diphenylpropene | 1,1-diphenylpropene |
| 98 | 1,1-diphenylpropene | 1,1-diphenylpropene |
| 99 | 1,1-diphenylpropene | 1,1-diphenylpropene |
| 100 | 1,1-diphenylpropene | 1,1-diphenylpropene |
| 101 | 4-propenylbiphenyl | 4-propenylbiphenyl |
| 102 | 4-propenylbiphenyl | 4-propenylbiphenyl |
| 103 | 4-propenylbiphenyl | 4-propenylbiphenyl |
| 104 | 4-propenylbiphenyl | 4-propenylbiphenyl |

TABLE 3-continued

| Compound | R³ | R⁴ | Ar³ | Ar¹ | Ar² |
|---|---|---|---|---|---|
| 105 | | | | | |
| 106 | | | | | |
| 107 | | | | | |
| 108 | | | | | |
| 69 | H | H | p-phenylene | phenyl | phenyl |
| 70 | H | H | p-phenylene | phenyl | 3-methylphenyl |
| 71 | H | H | p-phenylene | phenyl | 1-naphthyl |
| 72 | H | H | p-phenylene | phenyl | 4-(diphenylamino)phenyl |
| 73 | H | H | p-phenylene | phenyl | phenyl |
| 74 | H | H | p-phenylene | phenyl | 3-methylphenyl |
| 75 | H | H | p-phenylene | phenyl | 1-naphthyl |

TABLE 3-continued
| 76 | H | H |  | 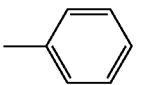 | 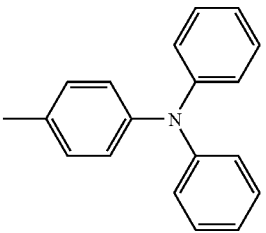 |
| 77 | H | H |  | 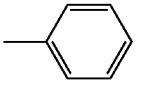 | 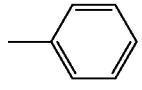 |
| 78 | H | H |  | 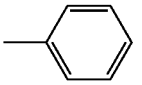 | 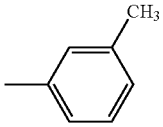 |
| 79 | H | H | 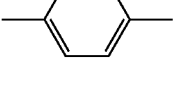 | 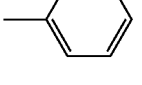 | 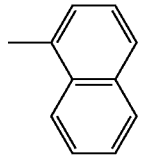 |
| 80 | H | H |  | 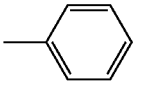 | 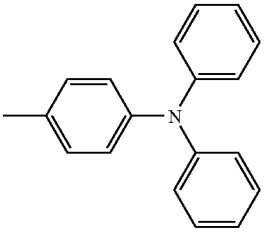 |
| 81 | H | H |  | 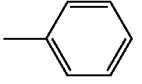 | 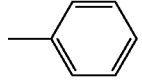 |
| 82 | H | H |  | 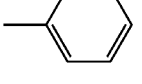 | 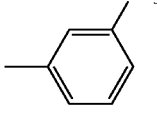 |
| 83 | H | H |  | 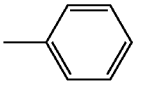 | 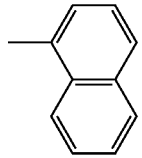 |
| 84 | H | H |  | 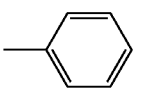 | 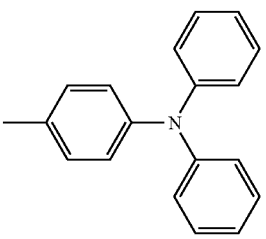 |

TABLE 3-continued
| 85 | H | H |  | 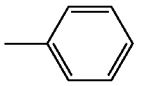 |  |
| 86 | H | H | 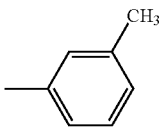 |  | 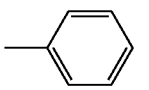 |
| 87 | H | H |  | 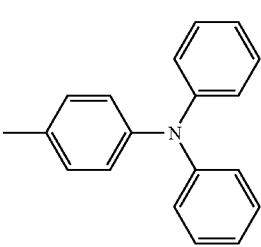 | 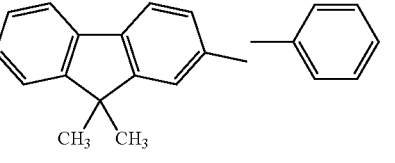 |
| 88 | H | H | 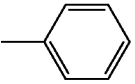 | 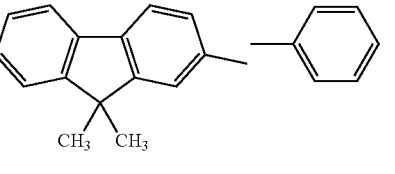 | 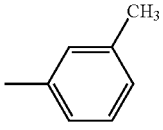 |
| 89 | H | H | 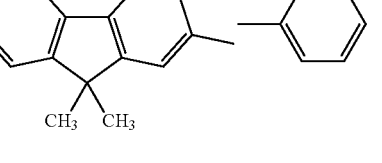 | 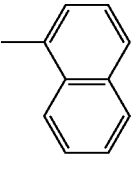 | 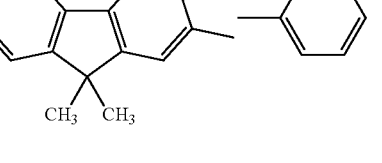 |
| 90 | H | H | 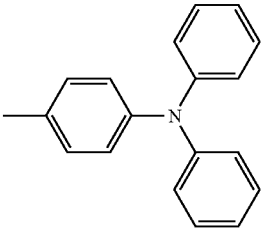 | 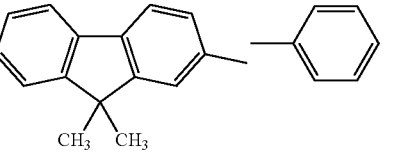 | 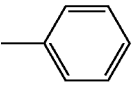 |
| 91 | H | H | | | |
| 92 | H | H | | | |
| 93 | H | H | | | |

TABLE 3-continued

| # | | | Ar (fluorene) | Ar' | Ar'' |
|---|---|---|---|---|---|
| 94 | H | H | 2,7-disubstituted 9,9-dimethylfluorene | phenyl | 3-methylphenyl |
| 95 | H | H | 2,7-disubstituted 9,9-dimethylfluorene | phenyl | 1-naphthyl |
| 96 | H | H | 2,7-disubstituted 9,9-dimethylfluorene | phenyl | 4-(diphenylamino)phenyl |
| 97 | H | H | 2,7-disubstituted 9,9-dimethylfluorene | phenyl | phenyl |
| 98 | H | H | 2,7-disubstituted 9,9-dimethylfluorene | phenyl | 3-methylphenyl |
| 99 | H | H | 2,7-disubstituted 9,9-dimethylfluorene | phenyl | 1-naphthyl |
| 100 | H | H | 2,7-disubstituted 9,9-dimethylfluorene | phenyl | 4-(diphenylamino)phenyl |
| 101 | H | H | 2,7-disubstituted 9,9-dimethylfluorene | phenyl | phenyl |

TABLE 3-continued
| 102 | H | H | 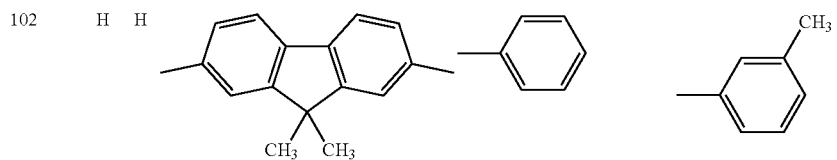 | | |
| --- | --- | --- | --- | --- | --- |
| 103 | H | H | 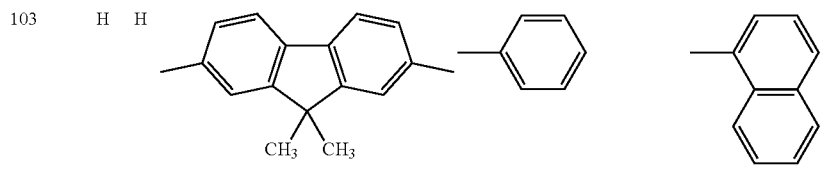 | | |
| 104 | H | H | 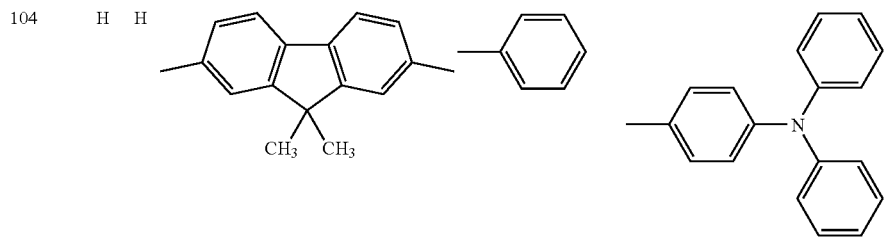 | | |
| 105 | H | H | 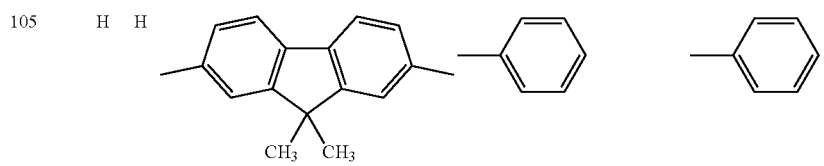 | | |
| 106 | H | H | 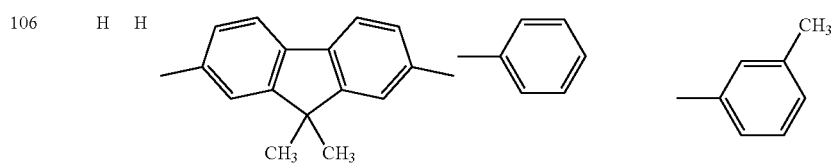 | | |
| 107 | H | H | 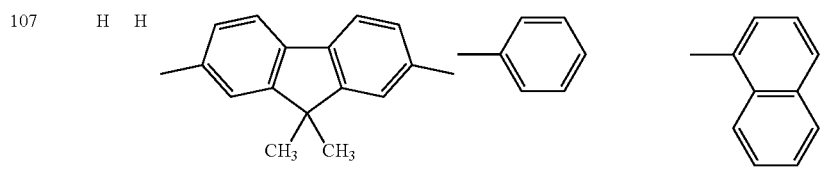 | | |
| 108 | H | H | 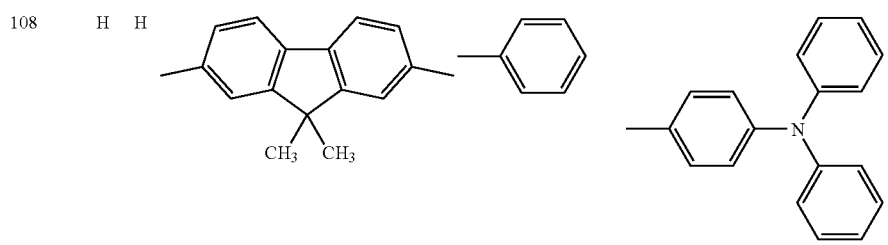 | | |

TABLE 4
| Compound | R¹ | R² |
|---|---|---|
| 109 | H | H |
| 110 | H | H |
| 111 | H | H |
| 112 | 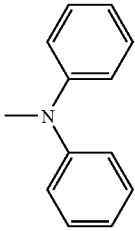 | 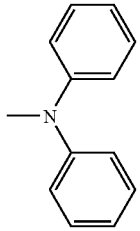 |
| 113 | H | H |
| 114 | H | H |
| 115 | H | H |
| 116 | 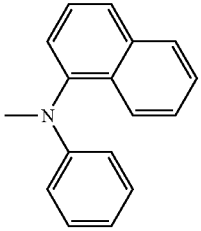 | 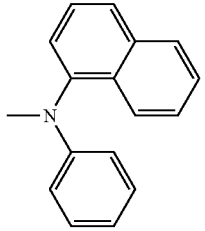 |
| 117 | 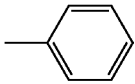 | 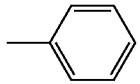 |
| 118 | 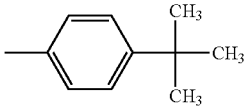 | 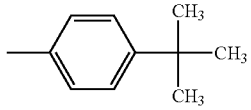 |
| 119 | 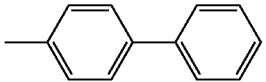 | 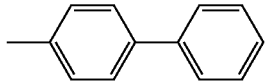 |
| 120 | 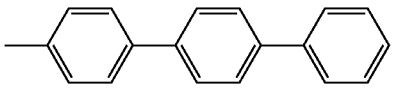 | 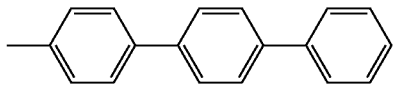 |
| 121 | 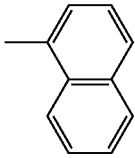 | 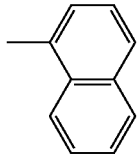 |
| 122 | 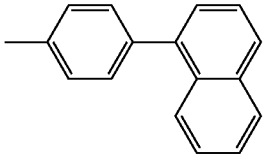 | 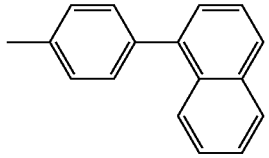 |

TABLE 4-continued
| | | |
|---|---|---|
| 123 | 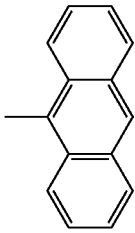 | 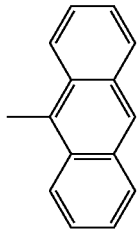 |
| 124 | 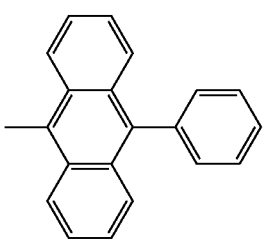 | 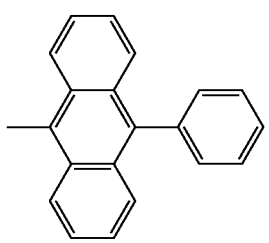 |
| 125 | 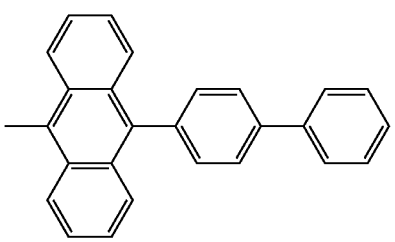 | 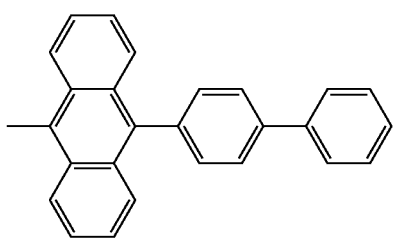 |
| 126 | H | H |
| 127 | H | H |
| 128 | H | H |
| 129 | 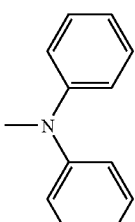 | 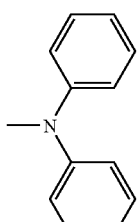 |
| 130 | H | H |
| 131 | H | H |
| 132 | H | H |
| 133 | 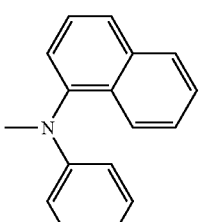 | 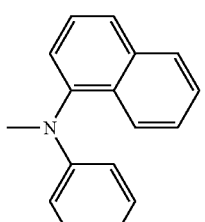 |
| 134 | 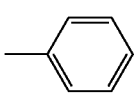 | 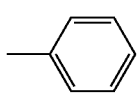 |
| 135 | 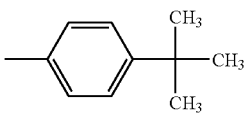 | 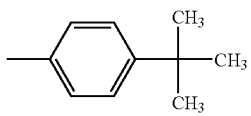 |

TABLE 4-continued
| 136 | 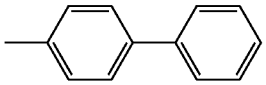 | 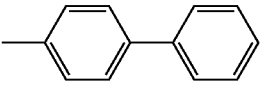 |
| 137 | 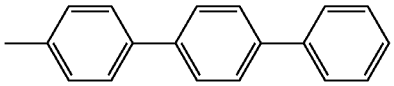 | 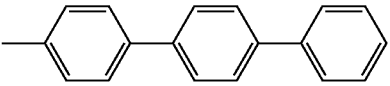 |
| 138 | 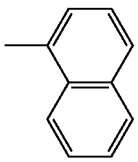 | 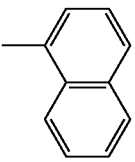 |
| 139 | 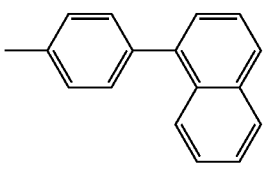 | 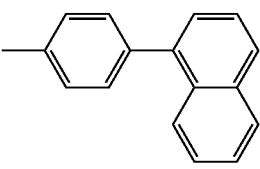 |
| 140 | 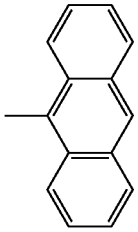 | 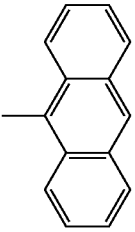 |
| 141 | 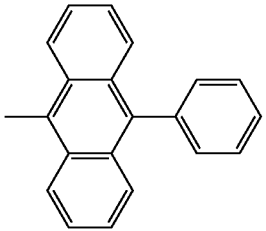 | 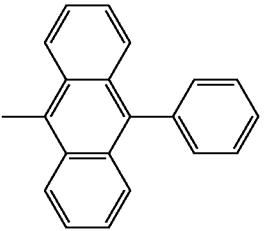 |
| 142 | 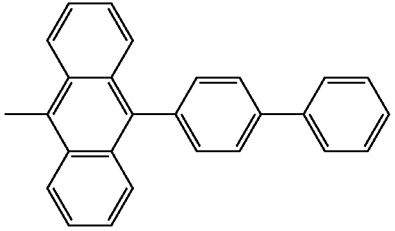 | 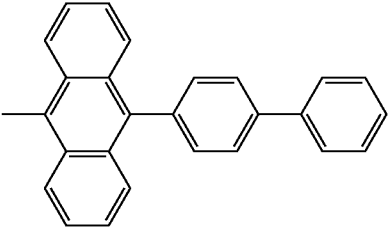 |
| 143 | 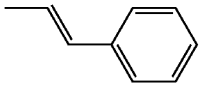 | 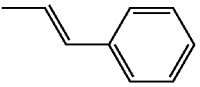 |
| 144 | 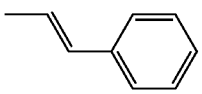 | 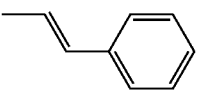 |
| 145 | 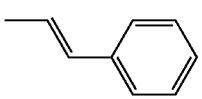 | 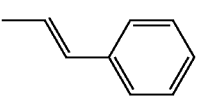 |

TABLE 4-continued
| 146 |  |  |
| --- | --- | --- |
| 147 | 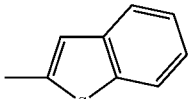 | 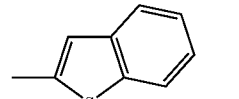 |
| 148 | 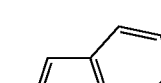 | 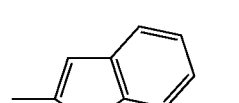 |
| 149 | 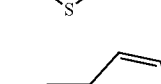 | 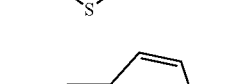 |
| 150 | 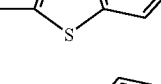 | 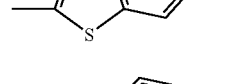 |
| 151 | 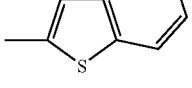 | 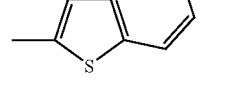 |
| 152 | 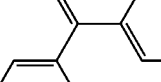 | 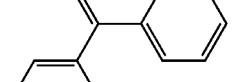 |
| 153 | 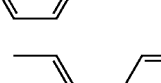 |  |
| 154 | 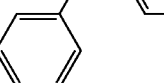 |  |
| 155 | 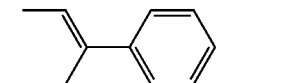 | 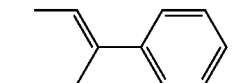 |

TABLE 4-continued

| | | | | | |
|---|---|---|---|---|---|
| 156 | styryl-biphenyl | | | styryl-biphenyl | |
| 157 | styryl-biphenyl | | | styryl-biphenyl | |
| 158 | styryl-biphenyl | | | styryl-biphenyl | |
| 159 | styryl-oxadiazole-biphenyl | | | styryl-oxadiazole-biphenyl | |
| 160 | styryl-oxadiazole-biphenyl | | | styryl-oxadiazole-biphenyl | |
| 161 | styryl-oxadiazole-biphenyl | | | styryl-oxadiazole-biphenyl | |
| 162 | styryl-oxadiazole-biphenyl | | | styryl-oxadiazole-biphenyl | |

| Compound | $R^3$ | $R^4$ | $Ar^3$ | $Ar^1$ | $Ar^2$ |
|---|---|---|---|---|---|
| 109 | H | H | biphenyl | phenyl | 1-naphthyl |
| 110 | H | H | biphenyl | phenyl | 3-methylphenyl |
| 111 | H | H | biphenyl | phenyl | phenyl |
| 112 | H | H | biphenyl | phenyl | phenyl |
| 113 | H | H | biphenyl | phenyl | 4-(diphenylamino)phenyl |

TABLE 4-continued
| 114 | H | H | 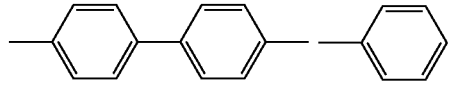 | 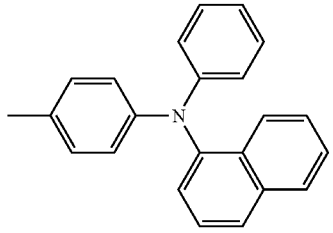 |
| 115 | H | H | 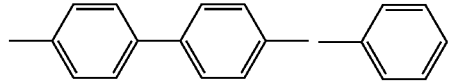 | 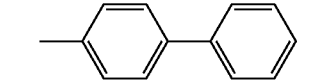 |
| 116 | H | H | 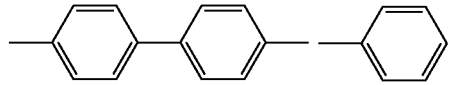 | 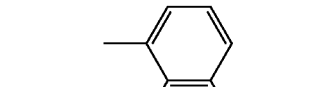 |
| 117 | H | H |  | 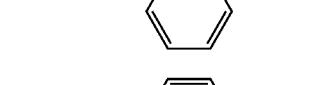 |
| 118 | H | H | 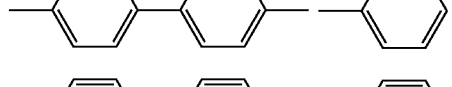 | 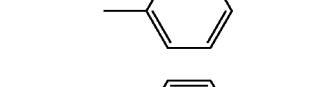 |
| 119 | H | H | 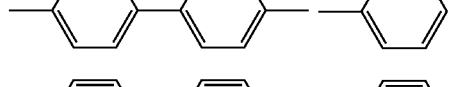 | 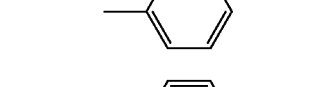 |
| 120 | H | H | 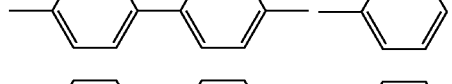 | 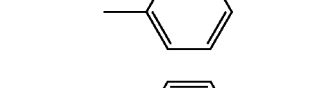 |
| 121 | H | H | 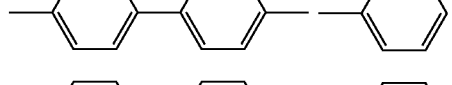 | 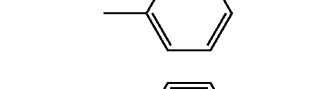 |
| 122 | H | H | 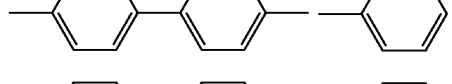 | 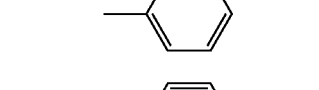 |
| 123 | H | H | 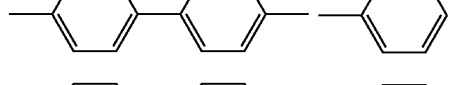 | 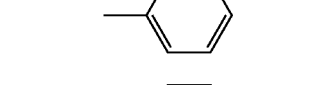 |
| 124 | H | H | 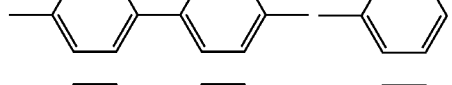 | 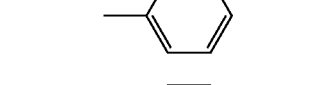 |
| 125 | H | H | 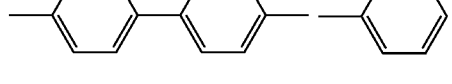 | 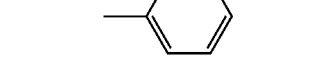 |
| 126 | 3-CH$_3$ | 3-CH$_3$ | 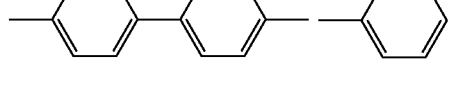 | 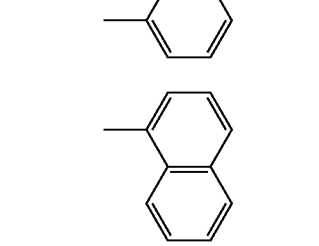 |

TABLE 4-continued
| 127 | 3-CH₃ | 3-CH₃ | 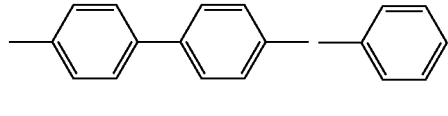 | 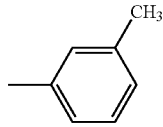 |
| 128 | 3-CH₃ | 3-CH₃ | 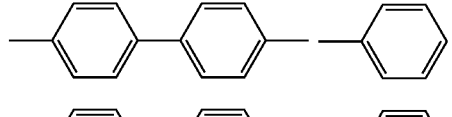 | 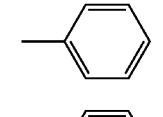 |
| 129 | 3-CH₃ | 3-CH₃ | 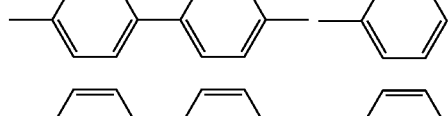 | 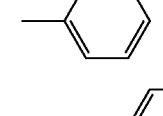 |
| 130 | 3-CH₃ | 3-CH₃ | 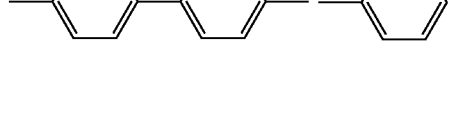 | 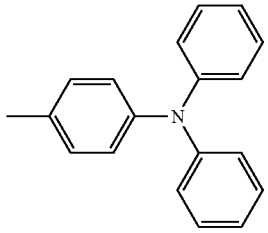 |
| 131 | 3-CH₃ | 3-CH₃ | 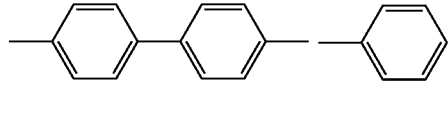 | 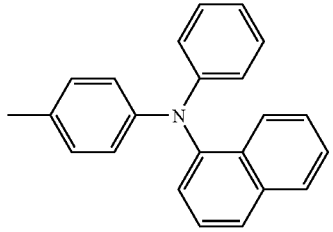 |
| 132 | 3-CH₃ | 3-CH₃ |  | 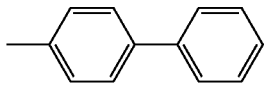 |
| 133 | 3-CH₃ | 3-CH₃ | 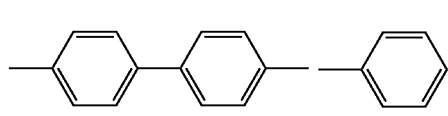 | 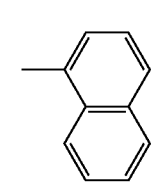 |
| 134 | 3-CH₃ | 3-CH₃ | 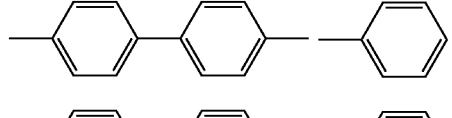 | 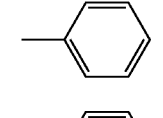 |
| 135 | 3-CH₃ | 3-CH₃ | 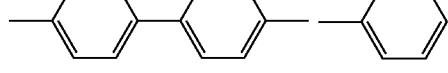 | 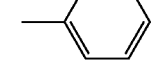 |
| 136 | 3-CH₃ | 3-CH₃ | 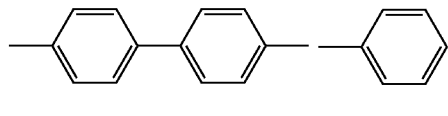 | 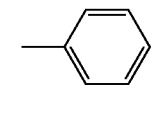 |
| 137 | 3-CH₃ | 3-CH₃ | 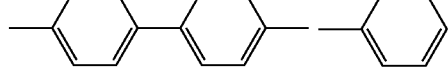 | 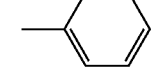 |
| 138 | 3-CH₃ | 3-CH₃ | 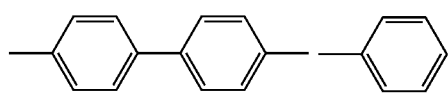 | 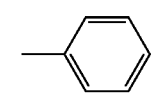 |

TABLE 4-continued

| 139 | 3-CH₃ | 3-CH₃ | (biphenyl-phenyl) | (phenyl) |
| 140 | 3-CH₃ | 3-CH₃ | (biphenyl-phenyl) | (phenyl) |
| 141 | 3-CH₃ | 3-CH₃ | (biphenyl-phenyl) | (phenyl) |
| 142 | 3-CH₃ | 3-CH₃ | (biphenyl-phenyl) | (phenyl) |
| 143 | H | H | (biphenyl-phenyl) | (phenyl) |
| 144 | H | H | (biphenyl-phenyl) | (3-methylphenyl) |
| 145 | H | H | (biphenyl-phenyl) | (1-naphthyl) |
| 146 | H | H | (biphenyl-phenyl) | (4-(diphenylamino)phenyl) |
| 147 | H | H | (biphenyl-phenyl) | (phenyl) |

TABLE 4-continued

| 148 | H | H | —C6H4—C6H4—C6H4— | 2,4-dimethylphenyl (3-methylphenyl) |
| 149 | H | H | —C6H4—C6H4—C6H4— | 1-naphthyl |
| 150 | H | H | —C6H4—C6H4—C6H4— | 4-(N,N-diphenylamino)phenyl |
| 151 | H | H | —C6H4—C6H4—C6H4— | phenyl |
| 152 | H | H | —C6H4—C6H4—C6H4— | 3-methylphenyl |
| 153 | H | H | —C6H4—C6H4—C6H4— | 1-naphthyl |
| 154 | H | H | —C6H4—C6H4—C6H4— | 4-(N,N-diphenylamino)phenyl |
| 155 | H | H | —C6H4—C6H4—C6H4— | phenyl |

TABLE 4-continued
| 156 | H | H | 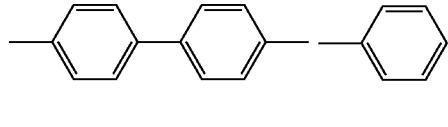 | 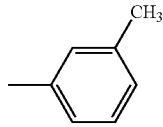 |
| 157 | H | H | 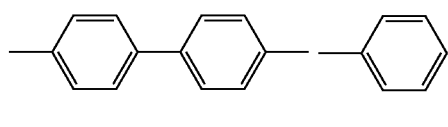 | 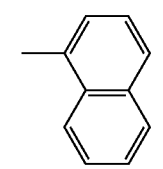 |
| 158 | H | H | 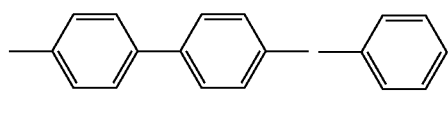 | 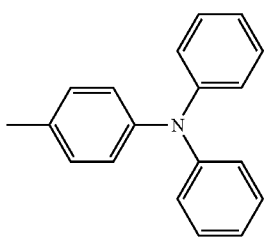 |
| 159 | H | H |  | 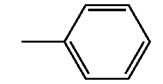 |
| 160 | H | H | 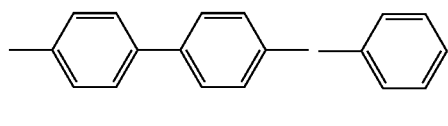 | 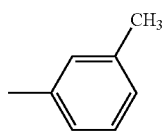 |
| 161 | H | H | 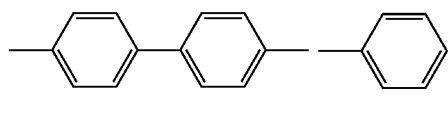 | 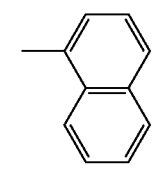 |
| 162 | H | H | 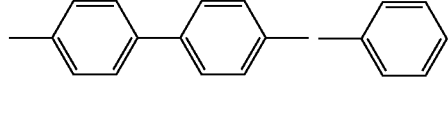 | 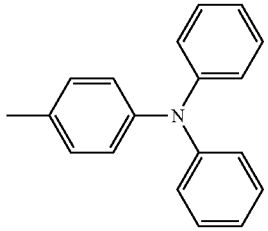 |

TABLE 5

| Compound | R¹ | R² | R³ | R⁴ | Ar³ | Ar¹ | Ar² |
|---|---|---|---|---|---|---|---|
| 163 | H | H | H | H | p-phenylene | N-carbazolyl | N-carbazolyl |
| 164 | diphenylamino-phenyl | diphenylamino-phenyl | H | H | p-phenylene | N-carbazolyl | N-carbazolyl |
| 165 | N-phenyl-N-(1-naphthyl)amino-phenyl | N-phenyl-N-(1-naphthyl)amino-phenyl | H | H | p-phenylene | N-carbazolyl | N-carbazolyl |
| 166 | phenyl | phenyl | H | H | p-phenylene | N-carbazolyl | N-carbazolyl |
| 167 | 4-(2-phenylpropan-2-yl)phenyl | 4-(2-phenylpropan-2-yl)phenyl | H | H | p-phenylene | N-carbazolyl | N-carbazolyl |

TABLE 5-continued

| Compound | R¹ | R² | R³ | R⁴ | Ar³ | Ar¹ Ar² |
|---|---|---|---|---|---|---|
| 168 | biphenyl | biphenyl | H | H | p-phenylene | carbazole |
| 169 | terphenyl | terphenyl | H | H | p-phenylene | carbazole |
| 170 | 1-naphthyl | 1-naphthyl | H | H | p-phenylene | carbazole |
| 171 | 1-naphthylphenyl | 1-naphthylphenyl | H | H | p-phenylene | carbazole |
| 172 | 9-anthryl | 9-anthryl | H | H | p-phenylene | carbazole |

TABLE 5-continued

| Compound | R¹ | R² | R³ | R⁴ | Ar³ | Ar¹ | Ar² |
|---|---|---|---|---|---|---|---|
| 173 | 10-methyl-9-phenylanthracen-9-yl | 10-methyl-9-phenylanthracen-9-yl | H | H | p-phenylene | N-carbazolyl | N-carbazolyl |
| 174 | 10-methyl-9-(biphenyl-4-yl)anthracen-9-yl | 10-methyl-9-(biphenyl-4-yl)anthracen-9-yl | H | H | p-phenylene | N-carbazolyl | N-carbazolyl |
| 175 | H | H | 3-CH₃ | 3-CH₃ | p-phenylene | N-carbazolyl | N-carbazolyl |
| 176 | N,N-diphenylamino | N,N-diphenylamino | 3-CH₃ | 3-CH₃ | p-phenylene | N-carbazolyl | N-carbazolyl |

TABLE 5-continued

| Compound | R¹ | R² | R³ | R⁴ | Ar³ | Ar¹ | Ar² |
|---|---|---|---|---|---|---|---|
| 177 | 1-naphthyl(phenyl)amino | 1-naphthyl(phenyl)amino | 3-CH₃ | 3-CH₃ | p-phenylene | carbazolyl | carbazolyl |
| 178 | phenyl | phenyl | 3-CH₃ | 3-CH₃ | p-phenylene | carbazolyl | carbazolyl |
| 179 | 4-(2-methyl-2-propyl)phenyl | 4-(2-methyl-2-propyl)phenyl | 3-CH₃ | 3-CH₃ | p-phenylene | carbazolyl | carbazolyl |
| 180 | biphenyl | biphenyl | 3-CH₃ | 3-CH₃ | p-phenylene | carbazolyl | carbazolyl |
| 181 | terphenyl | terphenyl | 3-CH₃ | 3-CH₃ | p-phenylene | carbazolyl | carbazolyl |

TABLE 5-continued

| Compound | R¹ | R² | R³ | R⁴ | Ar³ | Ar¹ | Ar² |
|---|---|---|---|---|---|---|---|
| 182 | 1-naphthyl | 1-naphthyl | 3-CH₃ | 3-CH₃ | p-phenylene | N-carbazolyl | N-carbazolyl |
| 183 | 4-(1-naphthyl)phenyl | 4-(1-naphthyl)phenyl | 3-CH₃ | 3-CH₃ | p-phenylene | N-carbazolyl | N-carbazolyl |
| 184 | 10-anthryl | 10-anthryl | 3-CH₃ | 3-CH₃ | p-phenylene | N-carbazolyl | N-carbazolyl |
| 185 | 10-(4-biphenyl)-9-anthryl | 10-(4-biphenyl)-9-anthryl | 3-CH₃ | 3-CH₃ | p-phenylene | N-carbazolyl | N-carbazolyl |
| 186 | | | 3-CH₃ | 3-CH₃ | p-phenylene | N-carbazolyl | N-carbazolyl |

The arylamine derivatives represented by the foregoing general formula (1) can be synthesized by reacting a di(haloaryl)fluorene represented by the following general formula (8) (wherein $R^1$ to $R^4$ and $Ar^3$ each represents the same substituent as described previously; and $X^1$ and $X^2$ each represents a chlorine atom, a bromine atom, or an iodine atom) with an amine compound represented by the following general formula (9) (wherein $Ar^1$ and $Ar^2$ each independently represents a substituted or unsubstituted aryl group or hetero-aromatic group, and $Ar^1$ and $Ar^2$ may form a nitrogen-containing heterocyclic ring together with the nitrogen atom to which $Ar^1$ and $Ar^2$ bond) in the presence of a base using a palladium catalyst.

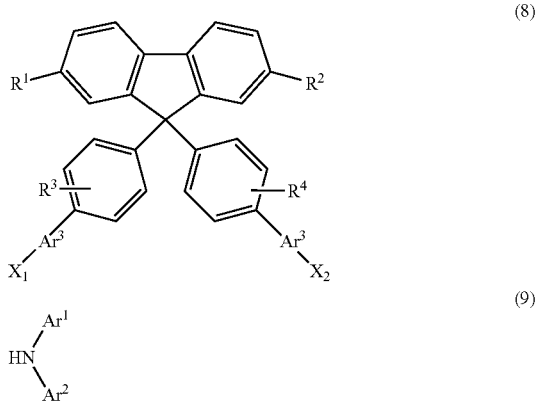

The palladium catalyst that is used in the invention comprises a palladium compound and a tertiary phosphine.

The palladium compound is not particularly limited. Examples thereof include tetravalent palladium compounds such as sodium hexachloropalladate(IV) tetrahydrate and potassium hexachloropalladate(IV); divalent palladium compounds such as palladium(II) chloride, palladium(II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraammninepalladium(II), dichloro(cycloocta-1,5-diene)palladium(II), and palladium(II) trifluoroacetate; and zerovalent palladium compounds such as tris(dibenzylideneacetone)dipalladium(0), tris(dibenzylideneacetone)dipalladium(0)-chloroform complex, and tetrakis(triphenylphosphine)palladium(0).

The amount of the palladium compound to be used is not particularly limited but is usually in the range of from 0.000001 to 20% by mole as reduced into palladium per mole of the di(haloaryl)fluorene derivative represented by the general formula (8). When the amount of the palladium compound to be used falls within the foregoing range, it is possible to synthesize the arylamine derivative with a high selectivity. For the sake of further enhancing the activity, taking into consideration the use of an expensive palladium compound, the amount of the palladium compound to be used is more preferably in the range of from 0.0001 to 5% by mole as reduced into palladium per mole of the di(haloaryl)fluorene derivative.

The tertiary phosphine that is used in combination with the palladium compound is not particularly limited. Examples include trialkylphosphines such as triethylphosphine, tricyclohexylphosphine, triisopropylphosphine, tri-n-butylphosphine, triisobutylphosphine, tri-sec-butylphosphine, and tri-tert-butylphosphine. Above all, for the sake of enhancing the selectivity of the arylamine derivative, tri-tert-butylphosphine is more preferable.

In the invention, the amount of the tertiary phosphine to be used is in the range of from 0.01 to 10,000 times by mole the palladium compound. When the amount of the tertiary phosphine to be used falls within the foregoing range, the selectivity of the arylamine derivative does not change. For the sake of further enhancing the activity, taking into consideration the use of an expensive tertiary phosphine, the amount of the tertiary phosphine to be used is more preferably in the range of from 0.1 to 10 times by mole the palladium compound.

In the invention, the palladium compound and the tertiary phosphine are essential, and a combination of the both compounds is added as a catalyst to the reaction system. As to the addition method, these compounds may be added individually to the reaction system, or may be added after previously adjusting them into a complex form.

The base that is used in the invention may be selected from inorganic bases and/or organic bases and is not particularly limited. Preferred examples include alkali metal alkoxides such as sodium methoxide, sodium ethoxide, potassium methoxide, potassium ethoxide, lithium tert-butoxide, sodium tert-butoxide, and potassium tert-butoxide. Such a base may be added to the reaction field as it stands, or may be provided in the reaction field by preparing it in situ from an alkali metal, an alkali metal hydride or an alkali metal hydroxide, and an alcohol.

The amount of the base used is preferably 0.5 times by mole or more against a hydrogen halide to be formed by the reaction. When the amount of the base is less than 0.5 times by mole, the yield of the arylamine derivative may possibly be lowered. Even when a large excess of the base is added, though the yield of the arylamine derivative does not change, the post-treatment operation after completion of the reaction becomes complicated. Accordingly, the amount of the base to be used is preferably in the range of from 1 to 5 times by mole.

In the invention, the reaction is usually carried out in the presence of an inert solvent. As to the solvent used, any solvents may be used without particular limitations so far as they do not remarkably hinder the present reaction. Examples of useful solvents include aromatic organic solvents such as benzene, toluene, and xylene; ether based organic solvents such as diethyl ether, tetrahydrofuran, and dioxane; acetonitrile; dimethylformamide; dimethyl sulfoxide; and hexamethyl phosphotriamide. Above all are more preferable aromatic organic solvents such as benzene, toluene, and xylene.

The reaction can be carried out in an atmosphere of an inert gas such as nitrogen and argon under atmospheric pressure or an elevated pressure.

The reaction temperature is in a range of from 20 to 300° C., and preferably from 50 to 200° C.

The reaction time is not constant according to the amounts of the di(haloaryl)fluorene derivative, amine compound, base and palladium catalyst and the reaction temperature but may be chosen within the range of from several minutes to 72 hours.

After completion of the reaction, the desired compound can be obtained through a usual treatment in the customary manner.

The compounds represented by the foregoing general formula (8) are useful as a synthetic intermediate of the novel arylamine derivative having a fluorene skeleton according to the invention. Especially, the case of the general formula (8) wherein Ar³ represents a phenylene group, and di(haloaryl)fluorene derivatives wherein each of R³ and R⁴ further represents a hydrogen atom, as represented by the following general formula (10), are preferable.

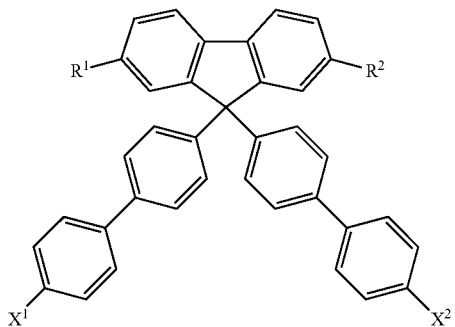

(10)

The case where $X^1$ and $X^2$ each represents a chlorine atom, and $R^1$ and $R^2$ each independently represents a hydrogen atom, an iodine group, a bromine atom, or an iodine atom is also useful as an intermediate of the arylamine derivative represented by the general formula (1).

The compounds represented by the general formula (8) can be synthesized by conventional methods. For example, they can be synthesized by reaction of an aromatic boronate with an aromatic halide or an aromatic triflate (usually called "Suzuki reaction") (N. Miyaura and A. Suzuki, *Chemical Reviews*, Vol. 95, 2457–2483 (1995)). Concretely, a fluorene derivative represented by the following general formula (11) is reacted with an aryl boronic acid compound represented by the following general formula (12) or (13) (wherein $X^3$ represents a halogen atom; $R^9$ represents a hydrogen atom, a methyl group, or an ethyl group; and $Ar^3$ represents a substituted or unsubstituted arylene group) in the presence of a base and a palladium catalyst. For example, the desired compound can be synthesized in the presence of an inorganic base such as sodium carbonate or/and sodium hydroxide using tetrakis(triphenylphosphine)palladium or the like as a catalyst. For the sake of synthesizing the di(haloaryl) fluorene represented by the foregoing general formula (8) with a good selectivity, it is preferable to use an aryl boronic acid compound represented by the following general formula (12).

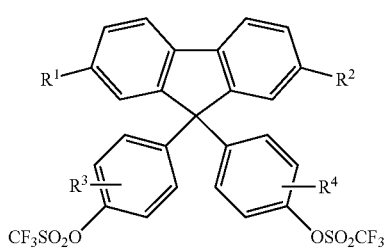

(11)

wherein $R^1$ to $R^4$ each represents the same substituent as described previously:

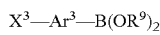

(12)

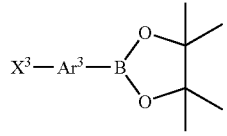

(13)

wherein $X^3$ represents a chlorine atom, and $R^9$ represents a hydrogen atom.

In addition, as another method, the compound of the foregoing general formula (8) can be similarly synthesized from a di(haloaryl)fluorene derivative represented by the following general formula (15), which is corresponding to the case of the general formula (8) wherein $R^1$ and $R^2$ each represents a bromine atom, and $X^1$ and $X^2$ each represents a chlorine atom, and a boronic acid derivative represented by the following general formula (16) or (17) according to the Suzuki reaction.

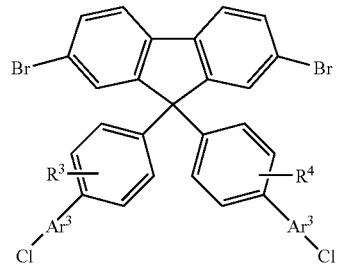

(15)

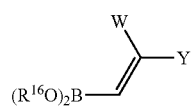

(16)

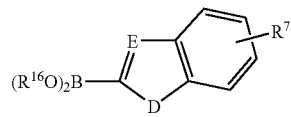

(17)

wherein D, E, Y, W and $R^7$ each represents the same substituent as described previously; and $R^{16}$ represents a hydrogen atom, a methyl group, or an ethyl group.

The novel arylamine derivatives having a fluorene skeleton according to the invention are different from conventional materials and have an amorphous structure at the time after the synthesis and hence, have an advantage such that the film stability is excellent. Accordingly, these compounds can be used not only as hole transport materials or luminescent materials of organic EL devices, electrophotographic receptors, etc. but also in any fields of organic photoconductive materials such as photoelectric transfer devices, solar batteries, and image sensors.

The novel arylamine derivatives having a fluorene skeleton represented by the forgoing general formula (1) according to the invention have a high Tg and have an amorphous structure and hence, are a material excellent in stability and durability as compared with the conventionally reported materials. They can be utilized as hole transport materials, luminescent materials, and the like of organic EL devices, electrophotographic receptors, etc.

The present invention will be described in more detail by reference to the following Examples, but it should be understood that the invention is not construed as being limited thereto.

SYNTHESIS EXAMPLE 1

Synthesis of 9,9-bis(4'-chloro-biphenyl-4-yl)fluorene 16 g of 9,9-bis[4-(trifluoromethylsulfonyl)phenyl]fluorene, 100 ml of tetrahydrofuran, 62 g of a 20% sodium carbonate aqueous solution, 8.54 g of 4-chlorophenylboronic acid, and 0.6 g of tetrakis(triphenylphosphine)palladium were placed in a 300 ml four-necked flask, and the mixture was heated at 70° C. The resulting mixture was aged at the same temperature for 18 hours, and the reaction mixture was then cooled to room temperature and subjected to liquid separation. An organic phase was washed with a saturated ammonium chloride aqueous solution and saturated salt water, and the resulting organic phase was concentrated and recrystallized from tetrahydrofuran to obtain 11.4 g of a white powder.

$^1$H-NMR (CDCl$_3$, ppm) δ: 7.91 (d, 2H), 7.39 to 7.60 (m, 11H)

$^{13}$C-NMR (CDCl$_3$, ppm) δ: 150.86, 145.22, 140.16, 139.06, 138.27, 133.28, 128.88, 128.66, 128.17, 127.88, 127.71, 126.81, 126.12, 120.35, 68.05

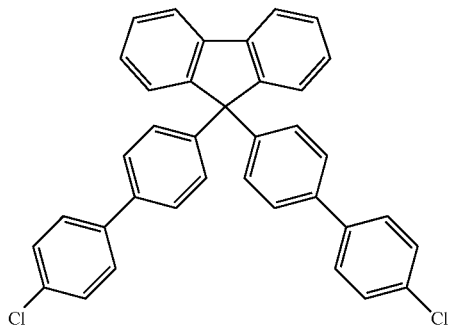

SYNTHESIS EXAMPLE 2

Synthesis of 9,9-bis(4'-chloro-biphenyl-4-yl)-2,7-dibromofluorene

In a 1 liter eggplant type flask, 34 g (63.0 mmoles) of 9,9-bis(4'-chloro-biphenyl-4-yl)fluorene was dissolved in 500 ml of CHCl$_3$, to which 0.68 g of iodine was then added. 50.3 g (314 mmoles) of bromine was added dropwise thereto at room temperature over 20 minutes, and after elevating the temperature to 40° C., the mixture was heated and stirred for 16 hours. After cooling, 350 g of 10% sodium thiosulfate was added dropwise to the reaction mixture such that the internal temperature did not exceed 30° C., to terminate the reaction, followed by liquid separation. An organic phase was washed with saturated salt water, dried over anhydrous Na$_2$SO$_4$, and then concentrated. 80 g of cyclohexane was added to the concentrate to deposit a colorless needle crystal. After filtration and drying, 35.8 g (yield: 81%) of the desired compound was isolated.

FDMS (flash desorption mass spectrometry)=697 $^1$-NMR (CDCl$_3$, ppm) δ: 7.21 to 7.72 (m) $^{13}$C-NMR (CDCl$_3$, ppm) δ: 152.65, 143.60, 138.88, 138.81, 138.07, 133.50, 131.17, 129.36, 128.94, 128.48, 128.20, 127.17, 122.02, 121.74, 65.19

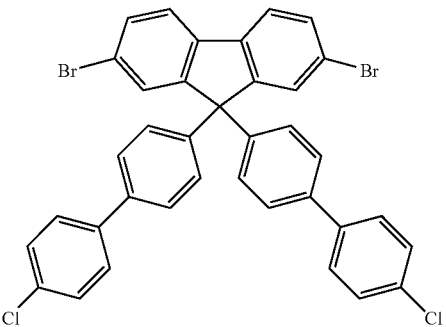

SYNTHESIS EXAMPLE 3

Synthesis of 9,9-bis(4'-bromo-biphenyl-4-yl)-2,7-dibromofluorene 15.9 g (33.8 mmoles) of 9,9-bis(biphenyl-4-yl)fluorene was dissolved in 200 mL of chloroform, to which 0.54 g of iron chloride was then added. 22.14 g (138 mmoles) of bromine was added dropwise to the mixture over 1.5 hours while maintaining the temperature of from room temperature to 50° C., followed by aging overnight. After cooling, 10% sodium thiosulfate was added dropwise thereto such that the internal temperature did not exceed 30° C., to terminate the reaction. An organic phase was washed with saturated salt water, dried over anhydrous Na$_2$SO$_4$, and subsequently concentrated to obtain a precipitate. The resulting precipitate was recrystallized from chloroform to isolate 15.3 g (yield: 57%) of a colorless needle crystal.

FDMS: 786 $^1$H-NMR (THF-d$_8$, ppm) δ: 7.81 (d, 2H), 7.51 to 7.66 (m, 10H), 7.29 (d, 2H) $^{13}$C-NMR (THF-d$_8$, ppm) δ: 153.79, 144.82, 140.30, 139.57, 139.18, 132.63, 131.97, 130.08, 129.33, 127.72, 122.99, 122.59, 122.21, 66.21

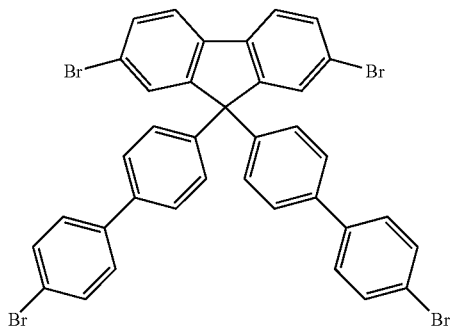

SYNTHESIS EXAMPLE 4

Synthesis of 9,9-bis(4'-chloro-biphenyl-4-yl)2,7-bis(4-biphenylyl)fluorene

A 100 ml eggplant type flask was charged with 5 g (7.17 mmoles) of 9,9-bis(4'-chloro-biphenyl-4-yl)-2,7-dibromofluorene obtained in Synthesis Example 2, 2.92 g (14.7 mmoles) of 4-biphenylylboronic acid, 45 ml of tetrahydrofuran, 12.9 g of a 10% sodium hydroxide aqueous solution, and 165 mg of tetrakis(triphenylphosphine), and the mixture was heated under reflux for 4 hours under a nitrogen gas stream. The reaction mixture was cooled and subjected to liquid separation, and the resulting organic phase was washed with a 10% ammonium chloride aqueous solution and saturated salt water. The organic phase was concentrated and then purified by silica gel chromatography and recrystallization to obtain 5.33 g (yield: 88%) a colorless powder. It was confirmed by FDMS and $^{13}$C-NMR that this powder was the desired compound.

FDMS: 844 $^{13}$C-NMR (CDCl$_3$, ppm) δ: 151.84, 145.02, 140.47, 140.32, 140.10, 139.88, 139.04, 138.95, 138.34, 133.24, 128.80, 128.75, 128.68, 128.11, 27.41, 127.32, 126.92, 126.81, 124.67, 120.71, 65.23

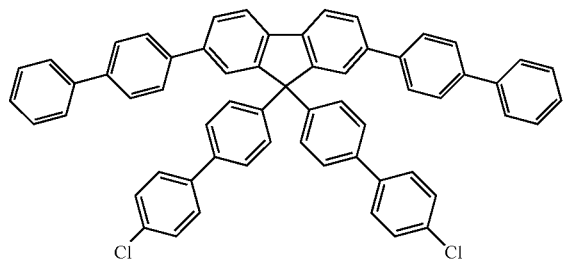

SYNTHESIS EXAMPLE 5

Synthesis of 9,9-bis(4'-chloro-biphenyl-4-yl)-2,7-bis(2-thianaphthenyl)fluorene

The same procedures as in Synthesis Example 4 were followed, except for using 2.62 g (14.7 mmoles) of thianaphthene-2-boronic acid in place of the 4-biphenylyl-boronic acid, to obtain 4.53 g (yield: 79%) of the desired compound.

FDMS: 804 $^{13}$C-NMR (THF-d$_8$, ppm) δ: 152.98, 145.58, 144.52, 141.63, 140.56, 140.09, 139.89, 139.19, 134.96, 133.77, 129.43, 129.40, 128.83, 127.56, 126.92, 125.15, 125.05, 124.45, 124.10, 122.65, 121.76, 120.53, 66.03

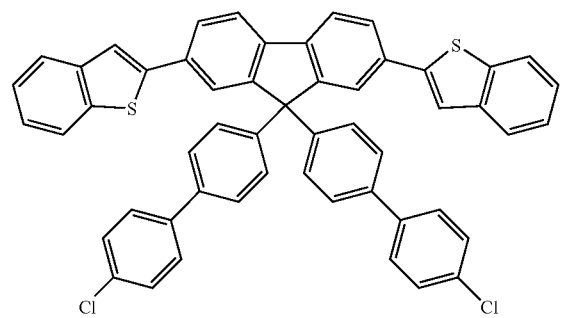

SYNTHESIS EXAMPLE 6

Synthesis of 9,9-bis(4'-chloro-biphenyl-4-yl)-2,7-bis(trans-2-phenylvinyl)fluorene The same procedures as in Synthesis Example 4 were followed, except for using 3.1 g of trans-2-phenylvinylboronic acid in place of the 4-biphenylylboronic acid, to obtain 3.84 g (yield: 72%) of the desired compound.

FDMS: 742 $^{13}$C-NMR (CDCl$_3$, ppm) δ: 151.77, 144.90, 139.42, 138.99, 138.40, 137.14, 137.10, 133.25, 128.82, 128.69, 128.60, 128.53, 128.14, 127.58, 126.94, 126.41, 124.06, 120.53, 64.91

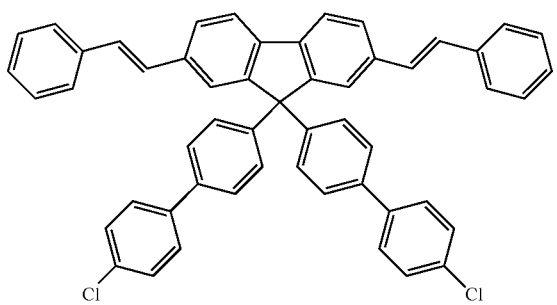

SYNTHESIS EXAMPLE 7

Synthesis of 9,9-bis(4'-chloro-biphenyl-4-yl)-2,7-bis(2,2-diphenylvinyl)fluorene)

20 g (111 mmoles) of 1,1-diphenylethylene was dissolved in 70 ml of cyclohexane, to which was then added dropwise 35 g (222 mmoles) of bromine at room temperature. The mixture was stirred at the same temperature for 20 hours and further heated under reflux for one hour. After cooling, the reaction mixture was washed with a sodium thiosulfate aqueous solution and saturated salt water, and an organic phase was separated by liquid separation. The organic phase was concentrated and subjected to Kugel distillation (at 145 to 148° C./0.6 Torr) to obtain 24 g (yield: 86%) of desired 1,1-diphenyl-2-bromoethylene. 4.8 g (18 mmoles) of 1,1-diphenyl-2-bromoethylene, 0.486 g (20 mmoles) of Mg, a small piece of iodine, and 100 mL of THF were added to a 300 ml eggplant type flask to prepare a Grignard reagent. The reaction mixture was cooled to −78° C., to which trimethoxyborane was then added dropwise while maintaining the same temperature. The mixture was stirred at room temperature for 2 hours, to which 2N hydrochloric acid was then added. An organic phase was treated to isolate desired 1,1-diphenylvinylboronic acid as a white powder in a yield of 35%. The same procedures as in Synthesis Example 4 were followed, except for using 3.28 g of 1,1-diphenylvinylboronic acid in place of the 4-biphenylylboronic acid, to obtain 3.77 g (yield: 72%) of the desired compound.

FDMS: 730 $^{13}$C-NMR (CDCl$_3$, ppm) δ: 150.76, 144.78, 143.24, 142.36, 140.29, 139.19, 138.46, 137.73, 136.96, 133.22, 130.13, 129.65, 128.92, 128.66, 128.44, 128.24, 128.13, 128.04, 127.45, 127.25, 126.94, 126.61, 119.80, 64.44

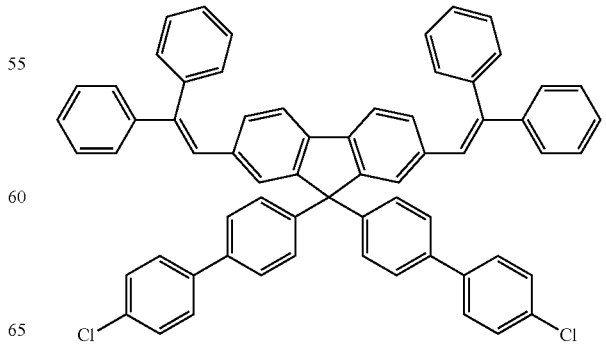

EXAMPLE 1

Synthesis of 9,9-bis[4-(N-phenyl-1-naphthylamino)-1,1'-biphenyl]fluorene (=Compound 1)

In a 50 ml three-necked flask, 3 g (5.6 mmoles) of 9,9-bis(4'-chloro-biphenyl-4-yl)fluorene, 2.56 g (11.7 mmoles) of N-phenyl-1-naphthylamine, and 1.28 g (13.3 mmoles) of sodium tert-butoxide were suspended in 40 ml of xylene, and the system was purged with nitrogen. Further, 3 mg of palladium acetate and 8 mg of tri-tert-butylphosphine were added to the suspension in a nitrogen atmosphere, followed by heating at 125° C. After aging at a prescribed temperature for 20 hours, the reaction mixture was cooled to room temperature. After adding 20 ml of water thereto, the mixture was subjected to extraction, and an organic phase was concentrated. The resulting organic phase was purified by silica gel chromatography (eluting solution: toluene) to obtain 4.9 g (yield: 97%) of a pale brown powder. It was confirmed by the elemental analysis and FDMS that this pale brown powder was the desired compound having the following structure.

FDMS: 904 Elemental analysis: Found: C; 91.1%, H; 5.6%, N; 3.3%. Calculated: C; 91.5%, H; 5.4%, N; 3.1%.

The glass transition temperature (Tg) of 9,9-bis[4-(N-phenyl-1-naphthylamino)-1,1'-biphenyl]fluorene as measured by differential scanning calorimetry (DSC) was 158° C. Besides, the measurement results of XRD and visible/ultraviolet and fluorescent spectra of NPD that is a general-purpose hole transport material and can be utilized as a blue luminescent material and Compound 1 are shown in Table 6. Compound 1 exhibited a high Tg as compared with NPD. Also, different from NPD, Compound 1 did not show a distinct diffraction peak and therefore, had an amorphous structure and exhibited a high value even in a blue fluorescent intensity.

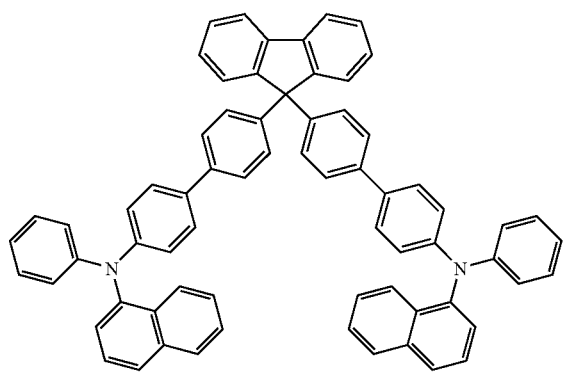

EXAMPLE 2

Synthesis of 9,9-bis[4-(N-m-tolyl-phenylamino)-1,1'-biphenyl]fluorene (=Compound 2)

The same procedures as in Example 1 were followed, except for using N-m-tolyl-aniline in place of the N-phenyl-1-naphthylamine, to obtain 3.85 g (yield: 82%) of a pale yellow powder. It was confirmed by the elemental analysis and FDMS that this pale yellow powder was the desired compound having the following structure. The physical property data are given in Table 6. Similar to Compound 1, this compound had a high Tg and had an amorphous structure and exhibited blue fluorescence.

FDMS: 832 Elemental analysis: Found: C; 90.9%, H; 5.7%, N; 3.4%. Calculated: C; 90.8%, H; 5.8%, N; 3.4%.

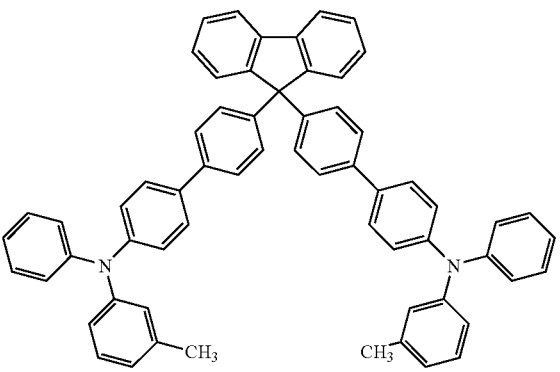

EXAMPLE 3

Synthesis of 9,9-bis[4-(diphenylamino)-1,1'-biphenyl]fluorene (=Compound 3)

The same procedures as in Example 2 were followed, except for using diphenylamine in place of the N-m-tolyl-aniline, to obtain 3.8 g (yield: 85%) of a pale yellow powder. It was confirmed by the elemental analysis and FDMS that this pale yellow powder was the desired compound having the following structure. The physical property data are given in Table 6. Similar to Compound 1, this compound had a high Tg and had an amorphous structure and exhibited blue fluorescence.

FDMS: 804 Elemental analysis: Found: C; 91.3%, H; 5.2%, N; 3.6%. Calculated: C; 91.0%, H; 5.5%, N; 3.5%. $^1$H-NMR (THF-d$_8$, ppm) δ: 7.83 (d, 2H), 6.95 to 7.47 (m, 34H) $^{13}$C-NMR (THF-d$_8$, ppm) δ: 152.09, 148.63, 148.03, 145.48, 141.16, 139.90, 135.63, 129.97, 129.33, 128.36, 128.27, 127.06, 125.19, 124.48, 123.69, 120.93, 66.01

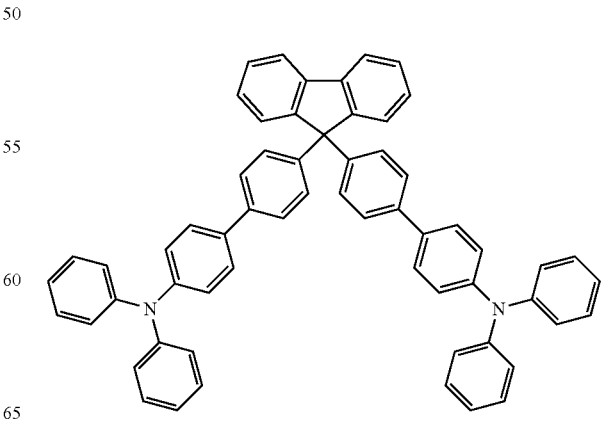

EXAMPLE 4

Synthesis of 2,7-diphenylamino-9,9-bis[4-(diphenylamino)-1,1'-biphenyl]fluorene (=Compound 4)

4 g (5.74 mmoles) of 9,9-bis(4'-chloro-biphenyl-4-yl)-2,7-dibromofluorene obtained in Synthesis Example 2, 2.65 g (27.6 mmoles) of sodium tert-butoxide, 4.08 g (24.1 mmoles) of diphenylamine, and 40 ml of xylene were placed in a 100 ml eggplant type flask, and the system was purged with nitrogen. A palladium catalyst prepared from 18 mg (0.02 mmoles) of tris(dibenzylideneacetone)palladium and 50 mg of tri-tert-butylphosphine was added thereto using a syringe, and the mixture was heated at 125° C. After aging at the same temperature for 16 hours, 40 g of water was added to the reaction mixture to terminate the reaction. After liquid separation, an organic phase was separated and concentrated to obtain 8.5 g of a viscous material. This viscous material was purified by silica gel chromatography to isolate 6.1 g of an amorphous substance. It was confirmed by the elemental analysis and FDMS that this amorphous substance was the desired compound having the following structure. The physical property data are given in Table 6. Similar to Compound 1, this compound had a high Tg and had an amorphous structure and exhibited blue fluorescence.

FDMS: 1138 Elemental analysis: Found: C; 89.4%, H; 5.6%, N; 5.0%. Calculated: C; 89.6%, H; 5.5%, N; 4.9%.

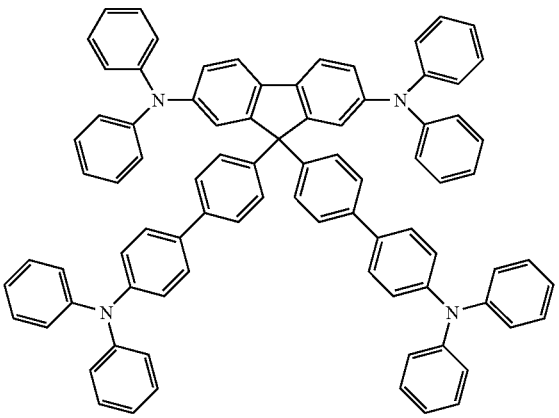

Table 6
| | Compound 1 | Compound 2 | Compound 3 | Compound 4 | Comparative Example |
|---|---|---|---|---|---|
| Structure | 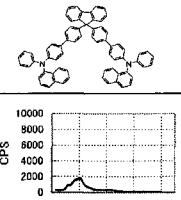 | 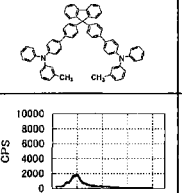 | 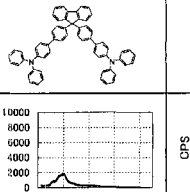 | 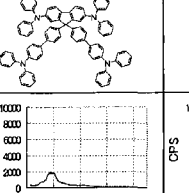 | 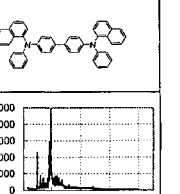 |
| XRD | | | | | |
| Tg /°C | 158 | 132 | 148 | 162 | 96 |
| Melting point /°C | Nil | Nil | Nil | Nil | 281 |
| UV–VIS[1] $\lambda$ max/nm | 324 | 336 | 334 | 342 | 340 |
| PL[1] $\lambda$ max/nm | 434 | 396 | 392 | 398 | 448 |
| Relative intensity ratio | 2.1 | 6.4 | 7.3 | 11.3 | 1 |
1) $c = 1.0 \times 10^{-6}$ mol/L(THF)

EXAMPLE 5

Synthesis of Compound 5

A 200 ml eggplant type flask was charged with 5.93 g (11 mmoles) of the compound obtained in Synthesis Example 1, 7.70 g (23 mmoles) of N,N,N'-triphenylphenylenediamine, 2.53 g (26 mmoles) of sodium tert-butoxide, and 48 g of o-xylene, to which were then added 5.2 mg of palladium acetate and 16 mg of tri-tert-butylphosphine under a nitrogen gas stream, and the mixture was heated and stirred at 125° C. for 20 hours. After cooling, 25 g of water was added to the reaction mixture and subjected to liquid separation, and an organic phase was separated. The resulting organic phase was concentrated and purified by silica gel chromatography (developing solution: toluene) to obtain the desired compound.
FDMS: 1138

EXAMPLE 6

Synthesis of Compound 11

A 100 ml eggplant type flask was charged with 2 g (2.36 mmoles) of 9,9-bis(4'-chloro-biphenyl-4-yl)-2,7-bis(4-biphenylyl)fluorene, 0.84 g (4.96 mmoles) of diphenylamine, 0.57 g of sodium tert-butoxide, and 20 ml of o-xylene, to which were then added 5 mg (0.022 mmoles) of palladium acetate and 4 mg of tri-tert-butylphosphine under a nitrogen gas stream, and the mixture was heated and stirred at 120° C. for 5 hours. After cooling, 20 g of water was added to the reaction mixture to terminate the reaction. After liquid separation, an organic phase was separated and concentrated, and then purified by silica gel chromatography to obtain 1.85 g (yield: 71%) of the desired compound.
The results of FDMS measurement, fluorescent spectrum (PL) in a tetrahydrofuran (THF) solution and visible/ultraviolet absorption spectrum (UV-VIS) of Compound 11 are shown in Table 7. It was confirmed from PL that Compound 11 was a blue fluorescent material.

EXAMPLE 7

Synthesis of Compound 69

The same procedures as in Example 6 were followed, except for using 1.75 g of the compound obtained in Synthesis Example 6 in place of the 9,9-bis(4'-chlorobiphenyl-4-yl)-2,7-bis(4-biphenylyl)fluorene, to isolate 1.7 g of the desired compound.
The results of FDMS measurement, fluorescent spectrum in a tetrahydrofuran (THF) solution and visible/ultraviolet absorption spectrum of Compound 69 are shown in Table 7. It was confirmed from PL that Compound 69 was a blue fluorescent material.

EXAMPLE 8

Synthesis of Compound 73

The same procedures as in Example 6 were followed, except for using 1.90 g of the compound obtained in Synthesis Example 5 in place of the 9,9-bis(4'-chlorobiphenyl-4-yl)-2,7-bis(4-biphenylyl)fluorene, to isolate 1.8 g of the desired compound.
The results of FDMS measurement, fluorescent spectrum in a tetrahydrofuran (THF) solution and visible/ultraviolet absorption spectrum of Compound 73 are shown in Table 7. It was confirmed from PL that Compound 73 was a blue fluorescent material.

EXAMPLE 9

Synthesis of Compound 77

The same procedures as in Example 6 were followed, except for using 1.90 g of the compound obtained in Synthesis Example 7 in place of the 9,9-bis(4'-chlorobiphenyl-4-yl)-2,7-bis(4-biphenylyl)fluorene, to isolate 1.8 g of the desired compound.
The results of FDMS measurement, fluorescent spectrum in a tetrahydrofuran (THF) solution and visible/ultraviolet absorption spectrum of Compound 77 are shown in Table 7. It was confirmed from PL that Compound 77 was a blue fluorescent material.
$^{13}$C-NMR (CDCl$_3$, ppm) δ: 64.48, 119.72, 122.89, 123.82, 124.41, 126.24, 127.03, 127.30, 127.47, 128.13, 128.36, 128.73, 129.24, 129.55, 130.12, 134.72, 136.86, 138.38, 138.49, 140.32, 142.23, 143.31, 143.94, 146.99, 147.63, 151.09

TABLE 7

| | Example | | | |
|---|---|---|---|---|
| | 6 | 7 | 8 | 9 |
| Compound | (11) | (69) | (73) | (77) |
| FDMS | 1108 | 1068 | 1008 | 1160 |
| UV-VIS λmax/nm[1)] | 340 | 347 | 343 | 340 |
| PL λmax/nm[1)] | 386,400 | 398,424 | 405,429 | 450 |
| Melting point (° C.) | Nil | 206 | Nil | Nil |
| Glass transition temperature (° C.) | 156 | 183 | 152 | 148 |

[1)] c = 1.0 × 10$^{-6}$ mole/L (THF)

With respect to Compounds 11, 69 and 77 obtained in Examples 6, 7 and 9, respectively, the PL measurement results of thin film are shown in FIG. 1. Even in the thin film, blue luminescence was observed similar to the solution.

EXAMPLE 10

Synthesis of Compound 20

The same procedures as in Synthesis Example 1 were followed, except for using 4,4'-(9-fluorenylidene) bis(1-trifluoromethylsulfonyl-3-methylphenyl) in place of the 9,9-bis[4-(trifluoromethylsulfonyl)phenyl]fluorene, to obtain a compound having the following structure. Further, the same procedures as in Example 3 were followed using the resulting compound and diphenylamine, to synthesize the desired Compound 20.
FDMS: 832

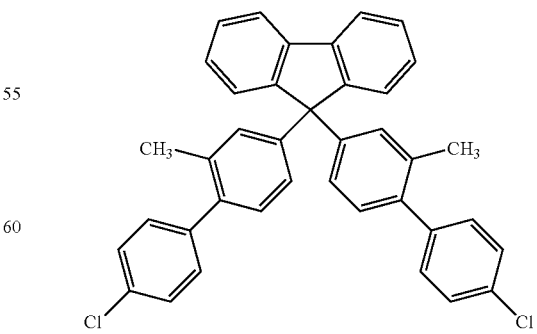

It should further be apparent to those skilled in the art that various changes in form and detail of the invention as shown and described above may be made. It is intended that such changes be included within the spirit and scope of the claims appended hereto.

What is claimed is:

1. An arylamine derivative represented by the general formula (1):

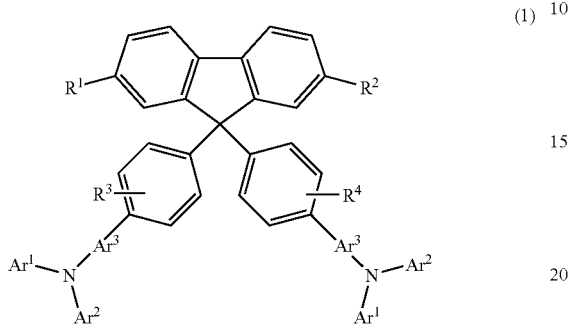

wherein $R^1$ to $R^4$ each independently represents a hydrogen atom, a linear, branched or cyclic alkyl group or alkoxy group, an aryl group, an aryloxy group, a halogen atom, an amino group, or a group represented by the following general formula (2), (3) or (4); $Ar^1$ and $Ar^2$ each independently represents a substituted or unsubstituted aryl group or hetero-aromatic group, and $Ar^1$ and $Ar^2$ may form a nitrogen-containing heterocyclic ring together with the nitrogen atom to which $Ar^1$ and $Ar^2$ bond; and $Ar^3$ represents a substituted or unsubstituted arylene group:

wherein Y represents a group represented by any one of the following general formulae (5a) to (5f); and W represents a hydrogen atom or a substituted or unsubstituted aryl group:

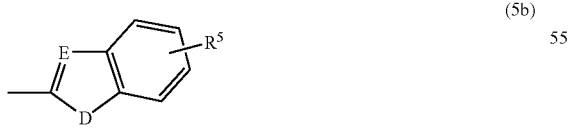

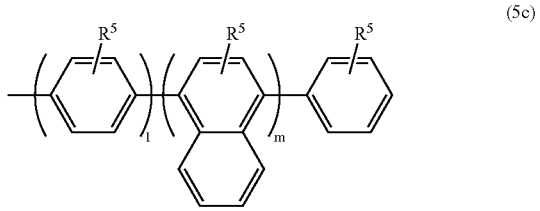

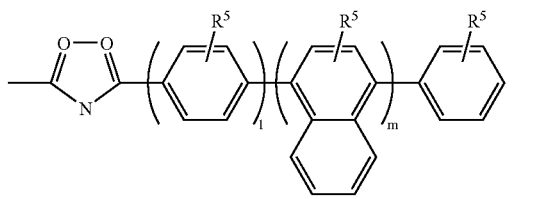

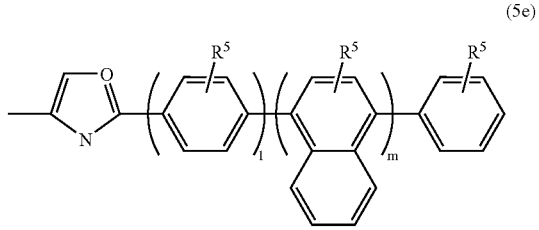

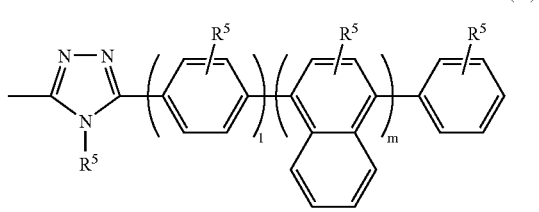

wherein $R^5$s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —$CR^6$— or a nitrogen atom; D represents any one of an oxygen atom, a nitrogen atom, or a sulfur atom; $R^6$ represents a hydrogen atom, a linear, branched or cyclic alkyl group, an aryl group, an amino group, a cyano group, a nitro group, a hydroxyl group, or a halogen atom; and l and m each represents an integer of from 0 to 4, satisfying the relation of (l+m)≦4:

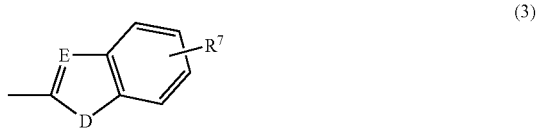

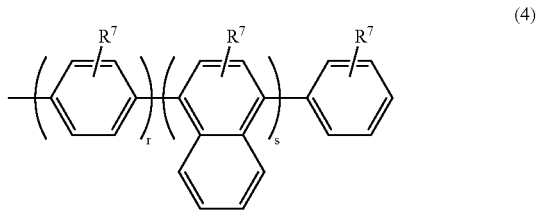

wherein $R^7$s' may be the same or different and each represents a hydrogen atom, a linear, branched or cyclic alkyl group or alkoxy group, an ester group, a hydroxyl group, a halogen atom, a cyano group, a nitro group, an amino group, an aryl group, or an aryloxy group; E represents —$CR^8$— or a nitrogen atom; $R^8$ represents a hydrogen atom, a linear, branched or cyclic alkyl group, an aryl group, an amino group, a cyano group, a nitro group, a hydroxyl group, or a halogen atom; D represents any one of an oxygen atom, a nitrogen atom, or a sulfur atom; and r and s each represents an integer of from 0 to 4, satisfying the relation of (r+s)≦4.

2. The arylamine derivative as claimed in claim 1, wherein in the general formula (1), at least one of $Ar^1$ and $Ar^2$ represents a substituted or unsubstituted condensed ring aromatic group.

3. The arylamine derivative as claimed in claim 2, wherein the condensed ring aromatic group represents a 1-naphthyl group, a 9-phenanthryl group, or a 2-fluorenyl group.

4. The arylamine derivative as claimed in claim 1, wherein in the general formula (1), $Ar^3$ represents a phenylene group.

5. The arylamine derivative as claimed in claim 4, wherein in the general formula (1), $R^3$ and $R^4$ each represents a hydrogen atom, and which is represented by the following general formula (6):

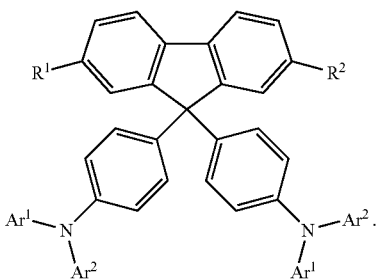

(6)

6. The arylamine derivative as claimed in claim 1, wherein in the formula (1), $R^1$ and $R^2$ each represents the group represented by the general formula (2); Y is represented by any one of the general formulae (5a) to (5c); and W represents a hydrogen atom or an unsubstituted phenyl group.

7. The arylamine derivative as claimed in claim 6, wherein Y represents any one of the following general formulae (7a) to (7c):

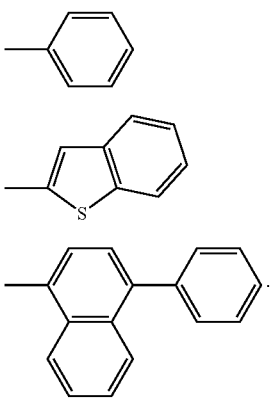

(7a)

(7b)

(7c)

8. The arylamine derivative according to claim 6, wherein W represents a hydrogen atom.

9. The arylamine derivative as claimed in claim 1, wherein in the general formula (1), $R^1$ and $R^2$ each represents the group represented by the general formula (3); E represents —CH—; and D represents a sulfur atom.

10. The arylamine derivative as claimed in claim 1, having an amorphous structure.

11. The arylamine derivative as claimed in claim 2, having an amorphous structure.

12. The arylamine derivative as claimed in claim 3, having an amorphous structure.

13. The arylamine derivative as claimed in claim 4, having an amorphous structure.

14. The arylamine derivative as claimed in claim 5, having an amorphous structure.

15. The arylamine derivative as claimed in claim 6, having an amorphous structure.

16. The arylamine derivative as claimed in claim 7, having an amorphous structure.

17. The arylamine derivative as claimed in claim 8, having an amorphous structure.

18. The arylamine derivative as claimed in claim 9, having an amorphous structure.

19. A process of producing the arylamine derivative as claimed in claim 1, which comprises reacting a di(haloaryl)fluorene represented by the following general formula (8):

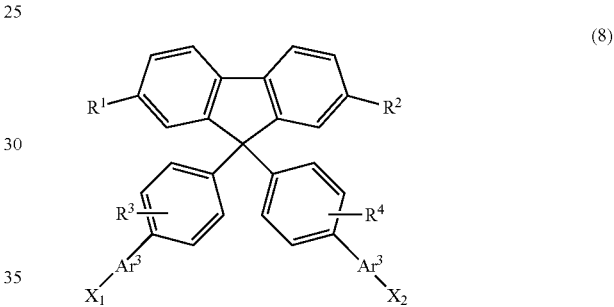

(8)

wherein $R^1$ to $R^4$ and $Ar^3$ each represents the same substituent as defined previously; and $X^1$ and $X^2$ each represents a chlorine atom, a bromine atom, or an iodine atom, and an amine compound represented by the following-general formula (9):

(9)

wherein $Ar^1$ and $Ar^2$ each represents a substituted or unsubstituted aryl group or hetero-aromatic group, and $Ar^1$ and $Ar^2$ may form a nitrogen-containing heterocyclic ring together with the nitrogen atom to which $Ar^1$ and $Ar^2$ bond, in the presence of a base using a palladium catalyst.

20. The process of producing the arylamine derivative as claimed in claim 19, wherein the palladium catalyst is a catalyst comprising a tertiary phosphine and a palladium compound.

21. The process of producing the arylamine derivative as claimed in claim 20, wherein the tertiary phosphine is tri-tert-butylphosphine.

* * * * *